US006204326B1

(12) United States Patent
Cook et al.

(10) Patent No.: US 6,204,326 B1
(45) Date of Patent: *Mar. 20, 2001

(54) PNA COMBINATORIAL LIBRARIES AND IMPROVED METHODS OF SYNTHESIS

(75) Inventors: Phillip Dan Cook, Vista; John Kiely, San Diego; Kelly Sprankle, Vista, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/131,270

(22) Filed: Aug. 7, 1998

Related U.S. Application Data

(63) Continuation of application No. 08/693,144, filed as application No. PCT/US95/02182 on Feb. 22, 1995, now Pat. No. 5,831,014, which is a continuation-in-part of application No. 08/200,742, filed on Feb. 23, 1994, now Pat. No. 5,539,083.

(51) Int. Cl.[7] .................................................. C08F 283/00

(52) U.S. Cl. ...................... 525/54.11; 530/334; 536/25.3

(58) Field of Search ................................... 530/300, 333, 530/334, 350, 335, 337; 536/22.1, 23.1, 24.1, 24.5, 25.3, 25.31; 525/54.1, 54.11

(56) References Cited

U.S. PATENT DOCUMENTS

| 3,803,118 | 4/1974 | Bennett | 260/112.5 |
| 5,539,083 | 7/1996 | Cook et al. | 530/333 |
| 5,831,014 * | 11/1998 | Cook et al. | 530/350 |

FOREIGN PATENT DOCUMENTS

| 43 31 011 | 3/1995 | (DE) . |
| 91/19735 | 12/1991 | (WO) . |
| 92/20702 | 11/1992 | (WO) . |
| 92/20703 | 11/1992 | (WO) . |
| 93/04204 | 3/1993 | (WO) . |
| 93/12129 | 6/1993 | (WO) . |
| 95/11909 | 5/1995 | (WO) . |
| 96/40709 | 12/1996 | (WO) . |

OTHER PUBLICATIONS

Achari et al., "Facing up to Membranes: Structure/Function Relationships in Phospholipases", Cold Spring Harbor Symp. Quant. Biol., 1987, 52, 441–452.*
Bomalaski et al., "Human Extracellular Recombinant Phospholipase $A_2$ Induces an Inflammatory Response in Rabbit Joints", J. Immunol., 1991, 146, 3904–3910.*
Burack et al., "Role of Lateral Phase Separation in the Modulation of Phospholipase $A_2$ Activity", Biochemistry, 1993, 32(2), 583–589.*
Campbell et al., "Inhibition of Phospholipase $A_2$; a Molecular Recognition Study", J. Chem. Soc., Chem. Commun., 1988, 1560–1562.*

Cho et al., "The Chemical Basis for Interfacial Activation of Monomeric Phospholipases $A_2$", J. Biol. Chem., 1988, 263(23), 11237–11241.*
Davidson et al., "1–Stearyl,2–Stearoylaminodeoxy Phosphatidylcholine, A Potent Reversible Inhibitor of Phospholipase $A_2$", Biochem. Biophys. Res. Commun., 1986, 137(2), 587–592.*
Dennis, "Phospholipases", The Enzymes Boyer, P.D. (Ed.), 1983, vol. XVI, 307–353.*
Ecker et al., "Pseudo–Half–Knot Formation with RNA", Science, 1992, 257, 958–961.*
Ecker et al., "Rational screening of oligonucleotide combinatorial libraries for drug discovery", Nucl. Acids Res., 1993, 21(8), 1853–1856.*
Egholm et al., "PNA hybridizes to complementary oligonucleotides obeying the Watson–Crick hydrogen–bonding rules", Nature, 1993, 365, 566–568.*
Epton et al., "Gel phase $^{13}C$ n.m.r. spectroscopy as an analytical method in solid (gel) phase peptide synthesis", Polymer, 1980, 21, 1367–1371.*
Geysen et al., "Strategies for epitope analysis using peptide synthesis", J. Immunol. Meth., 1987, 102, 259–274.*
Glaser et al., "Phospholipase $A_2$ enzymes: regulation and inhibition", TIPS Reviews, 1993, 14, 92–98.*
Grainger et al., "An enzyme caught in action: direct imaging of hydrolytic function and domain formation of phospholipase $A_2$ in phosphatidylcholine monolayers", FEBS Lett., 1989, 252(1,2), 73–82.*
Houghten et al., "Generation and use of synthetic peptide combinatorial libraries for basic research and drug discovery", Nature, 1991, 354, 84–86.*
Lombardo et al., "Cobra Venom Phospholipase $A_2$ Inhibition by Manoalide", J. Biol. Chem., 1985, 260(12), 7234–7240.*
Miyake et al., "The Novel Natural Product YM–26567–1 [(+)–trans–4–(3–dodecanoyl–2,4,6–trihydroxyphenyl)–7–hydroxy–2–(4–hydroxyphenyl)chroman]: A Competitive Inhibitor of Group II Phospholipase $A_2$", J. Pharmacol. Exp. Ther., 1992, 263, 1302–1307.*

(List continued on next page.)

Primary Examiner—John S. Brusca
Assistant Examiner—Thomas G. Larson
(74) Attorney, Agent, or Firm—Woodcock Washburn Kurtz Mackiewicz & Norris LLP

(57) ABSTRACT

New sub-monomer synthetic methods for the preparation of peptide nucleic acid oligomeric structures are disclosed that provide for the synthesis of both predefined sequence peptide nucleic acid oligomers as well as random sequence peptide nucleic acid oligomers. Further these methods also provide for the incorporation of peptide nucleic acid units or strings of such units with amino acids or strings of amino acids in chimeric peptide nucleic acid-amino acid compounds. Further disclosed are methods of making random libraries of peptide nucleic acids using the fully preformed monomers.

2 Claims, 8 Drawing Sheets

OTHER PUBLICATIONS

Noel et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.*

Ohlmeyer et al., "Complex synthetic chemical libraries indexed with molecular tags", *Proc. Natl. Acad. Sci. USA*, 1993, 90, 10922–10926.*

Owens et al., "The Rapid Identification of HIV Protease Inhibitors Through the Synthesis and Screening of Defined Peptide Mixtures", *Biochem. and Biophys. Res. Commun.*, 1991, 181(1), 402–408.*

Patel, "Marriage of convenience", *Nature*, 1993, 365, 490–492.*

Pruzanski et al., "Enzymatic Activity and Immunoreactivity of Extracellular Phospholipase $A_2$ in Inflammatory Synovial Fluids", *Inflammation*, 1992, 16(5), 451–457.*

Scott et al., "Interfacial Catalysis: The Mechanism of Phospholipase $A_2$", *Science*, 1990, 250, 1541–1546.*

Simon et al., "Peptoids: A modular approach to drug discovery", *Proc. Natl. Acad. Aci. USA*, 1992, 89, 9367–9371.*

Stewart and Young, eds., "Solid Phase Peptide Synthesis", 2nd Edition, 1984, p. 88.*

Vishwanath et al., "Edema–Inducing Activity of Phospholipase $A_2$ Purified from Human Synovial Fluid and Inhibition by Aristolochic Acid", *Inflammation*, 1988, 12(6), 549–561.*

Washburn et al., "Suicide–inhibitory Bifunctionally Linked Substrates (Siblinks) as Phospholipase $A_2$ Inhibitors", *J. Biol. Chem.*, 1991, 266(8), 5042–5048.*

Wery et al., "Structure of recombinant human rheumatoid arthritic synovial fluid phospholipase $A_2$ at 2.2A resolution", *Nature*, 1991, 352, 79–82.*

Westhof et al., "RNA pseudoknots", *Curr. Opin. Struct. Biol.*, 1992, 2, 327–333.*

Wyatt et al., "Combinatorially selected guanosine–quartet structure is a potent inhibitor of human immunodeficiency virus envelope–mediated cell fusion", *Proc. Natl. Acad. Sci. USA*, 1994, 91, 1356–1360.*

Yang et al., "Studies on the status of lysine residues in phospholipase $A_2$ from *Naja naja atra* (Taiwan cobra) snake venom", *J. Biochem.*, 1989, 262, 855–860.*

Yuan et al., "Synthesis and Evaluation of Phospholipid Analogues as Inhibitors of Cobra Venom Phospholipase $A_2$", *J. Am. Chem. Soc.*, 1987, 109(26), 8071–8081.*

Zuckermann et al., "Efficient Method for the Preparation of Peptoids [Oligo(N–substituted glycines)] by Submonomer Solid–Phase Synthesis", *J. Am. Chem. Soc.*, 1992, 114, 10646–10647.*

Nielsen P. et al., "Peptide Nucleic Acid (PNA). A DNA Mimic with a Peptide Backbone", *Bioconjugate Chem.*, 1994, 5, 3–7.*

Garnet, P. et al,. "Peptide–Based Nucleic Acid Surrogates Incorporating Ser[$CH_2B$]–Gly Subunits", *Tetra. Lett.*, 1993, 34, 1275–1278.*

Egholm, M. et al., "Peptide Nucleic Acids (PNA). Oligonucleotide Analogues with an Achiral Peptide Backbone", *J. Am. Chem Soc.*, 1992, 114, 1895–1897.*

Pischel et al., "Synthesis and Biological Activity of N–Substituted 5–Fluorouracil–1–Acetamides", *Coll. Czechoslovak Chem. Commun.*, 1982, 47, 2806–2813.*

* cited by examiner

PNA COMBINATORIAL LIBRARIES AND IMPROVED METHODS OF SYNTHESIS

CROSS REFERENCE TO RELATED APPLICATIONS

This application is a continuation of the U.S. National Phase Application Ser. No. 08/693,144, now U.S. Pat. No. 5,831,014, issued Nov. 3, 1998, filed Aug. 13, 1996, corresponding to International Application PCT/US 95/02182, filed Feb. 22, 1995, which is a continuation-in-part of U.S. application Ser. No. 08/200,742, filed Feb. 23, 1994, now U.S. Pat. No. 5,539,083, issued Jul. 23, 1996. Each of the foregoing applications are incorporated herein by reference in their entirety.

The contents of the foregoing patent application are incorporated herein by reference.

FIELD OF THE INVENTION

This invention is directed to improved synthetic processes for forming oligomeric peptide nucleic acids and combinatorial libraries of these peptide nucleic acids. The invention further includes new peptide nucleic acid chimeric structures. The processes of the invention utilize both monomeric and sub-monomeric synthons to form the oligomeric peptide nucleic acids having either random or predefined sequences of monomeric units. Each of the monomeric units includes a chemical moiety thereon for binding of the oligomeric structures to proteins, nucleic acids, and other biological targets. In preferred embodiments, compounds prepared via the processes of the invention act as inhibitors of enzymes such as phospholipase $A_2$ and are useful for the treatment of inflammatory diseases including atopic dermatitis and inflammatory bowel disease.

BACKGROUND OF THE INVENTION

Traditional processes of drug discovery involve the screening of complex fermentation broths and plant extracts for a desired biological activity or the chemical synthesis of many new compounds for evaluation as potential drugs. The advantage of screening mixtures from biological sources is that a large number of compounds are screened simultaneously, in some cases leading to the discovery of novel and complex natural products with activity that could not have been predicted otherwise. The disadvantages are that many different samples must be screened and numerous purifications must be carried out to identify the active component, often present only in trace amounts. On the other hand, laboratory syntheses give unambiguous products, but the preparation of each new structure requires significant amounts of resources. Generally, the de novo design of active compounds based on high resolution structures of enzymes has not been successful.

In order to maximize the advantages of each classical approach, new strategies for combinatorial unrandomization have been developed independently by several groups. Selection techniques have been used with libraries of peptides (see Geysen, H. M., Rodda, S. J., Mason, T. J., Tribbick, G. & Schoofs, P. G., *J. Immun. Meth.* 1987, 102, 259–274; Houghten, R. A., Pinilla, C., Blondelle, S. E., Appel, J. R., Dooley, C. T. & Cuervo, J. H., *Nature*, 1991, 354, 84–86; Owens, R. A., Gesellchen, P. D., Houchins, B. J. & DiMarchi, R. D., *Biochem. Biophys. Res. Commun.*, 1991, 181, 402–408), nucleic acids (see Wyatt, J. R., et al., *Proc. Natl. Acad. Sci. USA*, (in press); Ecker, D. J., Vickers, T. A., Hanecak, R., Driver, V. & Anderson, K., *Nucleic Acids Res.*, 1993, 21, 1853–1856) and nonpeptides (see Simon, R. J., et al., *Proc. Natl. Acad. Sci. USA*, 1992, 89, 9367–9371; Zuckermann, R. N., et al., *J. Amer. Chem. Soc.*, 1992, 114, 10646–10647; Bartlett, Santi, Simon, PCT WO91/19735; and Ohlmeyer, M. H., et al., *Proc. Natl. Acad. Sci. USA*, 1993, 90, 10922–10926). The techniques involve iterative synthesis and screening of increasingly simplified subsets of oligomers. Monomers or sub-monomers that have been utilized include amino acids and nucleotides, both of which are bifunctional. Utilizing these techniques, libraries have been assayed for activity in cell-based assays, in binding or inhibition of purified protein targets or otherwise.

A technique, called SURF (Synthetic Unrandomization of Randomized Fragments), involves the synthesis of subsets of oligomers containing a known residue at one fixed position and equimolar mixtures of residues at all other positions. For a library of oligomers four residues long containing three monomers (A, B, C), three subsets would be synthesized (NNAN, NNBN, NNCN, where N represents equal incorporation of each of the three monomers). Each subset is then screened in a functional assay and the best subset is identified (e.g. NNAN). A second set of libraries is synthesized and screened, each containing the fixed residue from the previous round, and a second fixed residue (e.g. ANAN, BNAN, CNAN). Through successive rounds of screening and synthesis, a unique sequence with activity in the assay can be identified. The SURFs technique is described in Ecker, D. J., Vickers, T. A., Hanecak, R., Driver, V. & Anderson, K., *Nucleic Acids Res.*, 1993, 21, 1853–1856. The SURF method is further described in PCT patent application WO 93/04204, the entire contents of which is herein incorporated by reference.

Peptide nucleic acids have been demonstrated to be useful surrogates for oligonucleotide in binding to both DNA and RNA nucleic acids (see Egholm et al., *Nature*, 1993, 365, 566–568 and reference cited therein and PCT applications WO 92/20702, WO 92/20703 and WO 93/12129). Additionally peptide nucleic acids have demonstrated the ability to effect strand displacement of double stranded DNA (see Patel, D. J., *Nature*, 1993, 365, 490–492 and references cited therein). It is not known to prepare peptide nucleic acid libraries however or to use peptide nucleic acid monomers in combinatorial techniques.

OBJECTS OF THE INVENTION

It is an object of this invention to provide new methods for the synthesis of peptide nucleic acid oligomeric structures.

It is a further object of this invention to provide sub-monomer methods for preparing peptide nucleic acid oligomeric structures.

It is a further object of this invention to provide methods of generating libraries of random sequence peptide nucleic acid oligomeric structures.

It is a further object of this invention to provide new chimeric oligomeric compounds formed of peptide nucleic acid units and amino acids units.

BRIEF DESCRIPTION OF THE INVENTION

In accordance with the above objects and other objects as will become evident from the remainder of this specification, there are provided novel processes for the synthesis of peptide nucleic acid oligomers. There is further provided chimeric compounds of the peptide nucleic acids and normal amino acids and process for making the same. In addition there are provided certain novel process for the preparation of libraries of peptide nucleic acid oligomers having random sequences and libraries of peptide nucleic acid oligomers having both random and fixed positions.

In a first process of the invention there is provided a method of adding further peptide nucleic acid units to an amine terminated peptide nucleic acid oligomer on a solid phase synthesis resin. The method includes treating the amine terminated oligomer on the solid phase synthesis resin with a bifunctional acetyl synthon to react a first reactive site of the bifunctional acetyl synthon with the terminal amine of the oligomer to form a resin bound oligomer having a monofunctional acetyl moiety thereon. The method further includes selecting an alkyldiamine synthon having the first of its amino functional groups in the form of a protected amino group and the other of its amino functions groups as a free amine. The method further includes treating the resin bound oligomer having the monofunctional acetyl moiety thereon with the alkyldiamine synthon to covalently bond the acetyl moiety and the free amine group of the alkyldiamine synthon forming a resin bound oligomer having an extension thereon where the extension includes a secondary amine and a protected amino group. The method further includes treating the oligomer having the extension thereon with an acetylnucleobase synthon to form an amide bond between the acetylnucleobase synthon and the secondary amine of the extension forming a new protected amine terminated resin bound peptide nucleic acid oligomer. The method further includes deprotecting the protected amino group of the resin bound extended oligomer and repeating further iteration of the method to further extend the oligomer. Upon completion of a product of the desired length, the synthesis is terminated.

In a further process of the invention there is provided a method of adding further random peptide nucleic acid units to an amine terminated peptide nucleic acid oligomer on a solid phase synthesis resin. The method includes treating the amine terminated oligomer on the solid phase synthesis resin with a bifunctional acetyl synthon to react a first reactive site of the bifunctional acetyl synthon with the terminal amine of the oligomer to form a resin bound peptide nucleic acid oligomer having a monofunctional acetyl moiety thereon. The method further includes selecting an alkyldiamine synthon having the first of its amino functional groups in the form of a protected amino group and the other of its amino functions groups as a free amine and treating the resin bound peptide nucleic acid oligomer having the monofunctional acetyl moiety thereon with the alkyldiamine synthon to covalently bond the acetyl moiety and the free amine group of the alkyldiamine synthon forming a resin bound peptide nucleic acid oligomer having an extension thereon where the extension includes a secondary amine and a protected amino group. The method further includes selecting a plurality of acetylnucleobase synthons wherein each of the synthons has a nucleobase that differs from the nucleobase of others of the synthons and treating the resin bound peptide nucleic acid oligomer having the extension thereon with the plurality of acetylnucleobase synthons to form an amide bond between an acetylnucleobase synthon and the secondary amine of the extension to extend the peptide nucleic acid oligomer with a new protected amine terminated resin bound peptide nucleic acid unit connected to other preceding peptide nucleic acid units. The method further includes deprotecting the protected amino group of the resin bound peptide nucleic acid unit to extend the peptide nucleic acid oligomer and repeating further iteration of the method to further extend the oligomer. Upon completion of a product of the desired length, the synthesis is terminated.

In an embodiment of the proceeding process, to fix one or more positions in the oligomeric compound, a preselected nucleobase carrying synthon is used during one of said repetitions in place of the plurality of synthon. When so used, this adds the preselected nucleobase synthon to said oligomer and thus fixes that position in the oligomeric compound.

In even a further process of the invention there is provided a method of adding further random peptide nucleic acid units to an amine terminated peptide nucleic acid oligomer on a solid phase synthesis resin. The method includes treating the amine terminated oligomer on the solid phase synthesis resin with a bifunctional acetyl synthon to react a first reactive site of the bifunctional acetyl synthon with the terminal amine of the oligomer to form a resin bound oligomer having a monofunctional acetyl moiety thereon. The method further includes selecting an alkyldiamine synthon having the first of its amino functional groups in the form of a protected amino group and the other of its amino functions groups as a free amine and treating the resin bound oligomer having the monofunctional acetyl moiety thereon with the alkyldiamine synthon to covalently bond the acetyl moiety and the free amine group of the alkyldiamine synthon forming a resin bound oligomer having an extension thereon where the extension includes a secondary amine and a protected amino group. The method further includes dividing the resin into portions. The method further includes selecting a plurality of acetylnucleobase synthons wherein each of the synthons has a nucleobase that differs from the nucleobase of others of the synthons and treating each of the portions of the resin bound oligomer having the extension thereon with one of the acetylnucleobase synthons to form an amide bond between the acetylnucleobase synthon and the secondary amine of the extension to extend the oligomer by the addition of a new protected amine terminated peptide nucleic acid unit connected to the oligomer. The method further includes combining each of the portions of resin together, deprotecting the protected amino group of the resin bound peptide nucleic acid oligomer and repeating further iteration of the method to further extend the oligomer. Upon completion of a product of the desired length, the synthesis is terminated.

In an embodiment of the proceeding process, to fix one or more positions in the oligomeric compound a preselected nucleobase carrying synthon is used during one of said repetitions, after dividing the resin, in place of the plurality of synthon. When so used, this adds the preselected nucleobase synthon to said oligomer in each of the portions of resin and thus fixes that position in the oligomeric compounds. The portions of the resin are not recombined but each is treated separately through further iterations of the method.

In even a further process of the invention there is provided a method of adding peptide nucleic acid units to one of an amine terminated peptide nucleic acid oligomer or an amine terminated amino acid oligomer on a solid phase synthesis resin. The method includes treating the amine terminated oligomer on the solid phase synthesis resin with a bifunctional acetyl synthon to react a first reactive site of the bifunctional acetyl synthon with the terminal amine of the oligomer to form a resin bound oligomer having a monofunctional acetyl moiety thereon. The method further includes selecting an alkyldiamine synthon having the first of its amino functional groups in the form of a protected amino group and the other of its amino functions groups as a free amine and treating the resin bound oligomer having the monofunctional acetyl moiety thereon with the alkyldiamine synthon to covalently bond the acetyl moiety and the free amine group of the alkyldiamine synthon forming a resin bound oligomer having an extension thereon where the extension includes a secondary amine and a protected amino group. The method further includes treating the oligomer having the extension thereon with an acetylnucleobase synthon to form an amide bond between the acetylnucleobase synthon and the secondary amine of the extension forming a new protected amine terminated resin bound peptide nucleic acid oligomer. The method further includes deprotecting the protected amino group of the resin bound extended oligomer and repeating further iteration of the method to further extend the oligomer. Upon completion of a product of the desired length, the synthesis is terminated.

In even a further process of the invention there is provided a method of preparing an oligomeric structure composed of mixed peptide nucleic acid units and amino acid units. The method includes selecting one of an amine terminated peptide nucleic acid structure or an amine terminated amino acid structure on a solid phase synthesis resin of the type wherein the structure has at least one peptide nucleic acid unit or at least one amino acid unit. The method further includes treating the amine terminated structure on the solid phase synthesis resin with a bifunctional acetyl synthon to react a first reactive site of the bifunctional acetyl synthon with the terminal amine of the structure to form a resin bound structure having a monofunctional acetyl moiety thereon. The method further includes selecting an alkyldiamine synthon having the first of its amino functional groups in the form of a protected amino group and the other of its amino functions groups as a free amine and treating the resin bound structure having the monofunctional acetyl moiety thereon with the alkyldiamine synthon to covalently bond the acetyl moiety and the free amine group of the alkyldiamine synthon forming a resin bound structure having an extension thereon where the extension includes a secondary amine and a protected amino group. The method further includes treating the structure having the extension thereon with an acetylnucleobase synthon to form an amide bond between the acetylnucleobase synthon and the secondary amine of the extension forming a new protected amine terminated resin bound peptide nucleic acid structure. The method further includes deprotecting the protected amino group of the resin bound extended structure and adding an amino acid monomeric unit to the deprotected amino group of the resin bound extended structure or repeating further iteration of the method to further extend the structure. Upon completion of a product of the desired length, the synthesis is terminated.

In each of the above processes, preferably the alkydiamine synthon is a $C_2$–$C_6$ alkyldiamine. The most preferred alkyldiamine is ethylenediamine.

In even a further process of the invention there is provided a method of adding further peptide nucleic acid units to an amine terminated peptide nucleic acid oligomer on a solid phase synthesis resin. The method includes treating the amine terminated oligomer on the solid phase synthesis resin with a bifunctional acetyl synthon to react a first functional group of the bifunctional acetyl synthon with the terminal amine of the oligomer to form a resin bound oligomer having a monofunctional acetyl moiety thereon. The method further includes selecting an alkyldiamine-acetylnucleobase synthon wherein the first amine group of the synthon is present as a protected amino group and the other amine group of the synthon is incorporated into a secondary amide group with the acetylnucleobase portion of the synthon and treating the resin bound oligomer having the monofunctional acetyl moiety thereon with the alkyldiamine-acetylnucleobase synthon to covalently bond the acetyl moiety and the secondary amide group of the alkyldiamine-acetylnucleobase synthon forming a resin bound extended oligomer having a protected amino group thereon. The method further includes deprotecting the protected amino group of the resin bound extended oligomer to form a new amine terminated resin bound oligomer and repeating further iteration of the method to further extend the oligomer. Upon completion of a product of the desired length, the synthesis is terminated.

In even a further process of the invention there is provided a method of adding further random peptide nucleic acid units to an amine terminated peptide nucleic acid oligomer on a solid phase synthesis resin. The method includes treating the amine terminated oligomer on the solid phase synthesis resin with a bifunctional acetyl synthon to react a first reactive site of the bifunctional acetyl synthon with the terminal amine of the oligomer to form a resin bound peptide nucleic acid oligomer having a monofunctional acetyl moiety thereon. The method further includes selecting a plurality of alkyldiamine-acetylnucleobase synthons wherein in each such synthon the nucleobase is different from the nucleobase in others of the plurality of synthons and in each such synthon the first amine group of the synthon is present as a protected amino group and the other amine group of the synthon is incorporated into a secondary amide group with the acetylnucleobase portion of the synthon. The method further includes treating the resin bound peptide nucleic acid oligomer having the monofunctional acetyl moiety thereon with the plurality of alkyldiamine-acetylnucleobase synthons to extend the peptide nucleic acid oligomer by the addition of a new protected amine terminated resin bound peptide nucleic acid unit. The method further includes deprotecting the protected amino group of the resin bound peptide nucleic acid unit to extend resin bound peptide nucleic acid oligomer and repeating further iteration of the method to further extend the oligomer. Upon completion of a product of the desired length, the synthesis is terminated.

In an embodiment of the proceeding process, to fix one or more positions in the oligomeric compound, a preselected nucleobase carrying synthon is used during one of said repetitions in place of the plurality of synthon. When so used, this adds the preselected nucleobase synthon to said oligomer and thus fixes that position in the oligomeric compounds.

In even a further process of the invention there is provided a method of adding further random peptide nucleic acid units to an amine terminated peptide nucleic acid oligomer on a solid phase synthesis resin. The method includes treating the amine terminated oligomer on the solid phase synthesis resin with a bifunctional acetyl synthon to react a first reactive site of the bifunctional acetyl synthon with the terminal amine of the unit to form a resin bound peptide nucleic acid oligomer having a monofunctional acetyl moiety thereon. The method further includes selecting a plurality of alkyldiamine-acetylnucleobase synthons wherein in each such synthon the nucleobase is different from the nucleobase in others of the plurality of synthons and in each such synthon the first of the amine group of the synthon is present as a protected amino group and the other amine group of the synthon is incorporated into a secondary amide group with the acetylnucleobase portion of the synthon. The method further includes dividing the resin into portions and treating each of the portions of the resin bound peptide nucleic acid oligomer having the monofunctional acetyl moiety thereon with one of the plurality of alkyldiamine-acetylnucleobase synthons to extend the peptide nucleic acid oligomer by the addition of a protected amine terminated resin bound peptide nucleic acid unit. The method further includes combining each of the portions of resin together and deprotecting the protected amino group of the resin bound peptide nucleic acid unit to extend the peptide nucleic acid oligomer. The method further includes repeating further iteration of the method to further extend the oligomer. Upon completion of a product of the desired length, the synthesis is terminated.

In an embodiment of the proceeding process, to fix one or more positions in the oligomeric compound a preselected nucleobase carrying synthon is used during one of said repetitions, after dividing the resin, in place of the plurality of synthon. When so used, this adds the preselected nucleobase synthon to said oligomer in each of the portions of resin and thus fixes that position in the oligomeric compounds. The portions of the resin are not recombined but each is treated separately through further iterations of the method.

In even a further process of the invention there is provided a method of adding peptide nucleic acid units to one of an amine terminated peptide nucleic acid oligomer or an amine terminated amino acid oligomer on a solid phase synthesis resin. The method includes treating the amine terminated oligomer on the solid phase synthesis resin with a bifunctional acetyl synthon to react a first functional group of the bifunctional acetyl synthon with the terminal amine of the oligomer to form a resin bound oligomer having a monofunctional acetyl moiety thereon. The method further includes selecting an alkyldiamine-acetylnucleobase synthon wherein the first of the amine group of the synthon is present as a protected amino group and the other amine group of the synthon is incorporated into a secondary amide group with the acetylnucleobase portion of the synthon. The method further includes treating the resin bound oligomer having the monofunctional acetyl moiety thereon with the alkyldiamine-acetylnucleobase synthon to covalently bond the acetyl moiety and the secondary amide group of the alkyldiamine-acetylnucleobase synthon forming a resin bound extended oligomer having a protected amino group thereon. The method further includes deprotecting the protected amino group of the resin bound extended oligomer to form a new amine terminated resin bound oligomer and repeating further iteration of the method to further extend the oligomer. Upon completion of a product of the desired length, the synthesis is terminated.

In even a further process of the invention there is provided a method of preparing an oligomeric structure composed of mixed peptide nucleic acid units and amino acid units. The method includes selecting one of an amine terminated peptide nucleic acid structure or an amine terminated amino acid structure on a solid phase synthesis resin and where the structure has at least one peptide nucleic acid unit or at least one amino acid unit and treating the amine terminated structure on the solid phase synthesis resin with a bifunctional acetyl synthon to react a first functional group of the bifunctional acetyl synthon with the terminal amine of the structure to form a resin bound structure having a monofunctional acetyl moiety thereon. The method further includes selecting an alkyldiamine-acetylnucleobase synthon wherein the first amine group of the synthon is present as a protected amino group and the other amine group of the synthon is incorporated into a secondary amide group with the acetylnucleobase portion of the synthon and treating the resin bound structure having the monofunctional acetyl moiety thereon with the alkyldiamine-acetylnucleobase synthon to covalently bond the acetyl moiety and the secondary amide group of the alkyldiamine-acetylnucleobase synthon forming a resin bound extended structure having a protected amino group thereon. The method further includes deprotecting the protected amino group of the resin bound extended structure to form a new amine terminated resin bound structure and adding an amino acid monomeric unit to the deprotected amino group of the resin bound extended structure to extend the structure or repeating further iteration of the method to further extend the structure. Upon completion of a product of the desired length, the synthesis is terminated.

In each of the immediately preceeding processes, preferably the alkyldiamine portion of the alkyldiamine-acetylnucleobase synthon is a $C_2$–$C_6$ alkyldiamine. The most preferred alkyldiamine is ethylenediamine.

In even a further process of the invention there is provided a method of adding further peptide nucleic acid units to an amine terminated peptide nucleic acid oligomer on a solid phase synthesis resin. The method includes treating the amine terminated oligomer on the solid phase synthesis resin with a 1-(2-carbonylmethylnucleobase)-3-oxo-morpholine synthon to form a resin bound oligomer having a N-[2-(nucleobase)acetyl]-N-(hydroxyethyl)glycyl terminus moiety thereon. The method further includes treating the resin bound oligomer have the terminus moiety to convert the terminus moiety to an amine terminated N-[2-(nucleobase)acetyl]-N-(aminoethyl)glycyl terminus moiety thereby extending the oligomer by an amine terminated peptide nucleic acid unit and repeating further iteration of the method to further extend the oligomer. Upon completion of a product of the desired length, the synthesis is terminated.

In even a further process of the invention there is provided a method of adding further random peptide nucleic acid units to an amine terminated peptide nucleic acid oligomer on a solid phase synthesis resin. The method includes selecting a plurality of 1-(2-carbonylmethylnucleobase)-3-oxo-morpholine synthons wherein each of the synthons has a nucleobase that differs from the nucleobase of others of the synthons and treating the amine terminated unit on the solid phase synthesis resin with the plurality of synthons forming resin bound oligomers having N-[2-(nucleobase)acetyl]-N-(hydroxyethyl)glycyl terminus moieties thereon. The method further includes treating the resin bound oligomers have the terminus moieties to convert the terminus moieties to amine terminated N-[2-(nucleobase)acetyl]-N-(aminoethyl)glycyl terminus moieties thereby extending the oligomers by one amine terminated peptide nucleic acid unit and repeating further iteration of the method to further extend the oligomer. Upon completion of a product of the desired length, the synthesis is terminated.

In an embodiment of the proceeding process, to fix one or more positions in the oligomeric compound, a preselected nucleobase carrying synthon is used during one of said repetitions in place of the plurality of synthon. When so used, this adds the preselected nucleobase synthon to said oligomer and thus fixes that position in the oligomeric compounds.

In even a further process of the invention there is provided a method of adding further random peptide nucleic acid units to an amine terminated peptide nucleic acid oligomer on a solid phase synthesis resin. The method includes selecting a plurality of 1-(2-carbonylmethylnucleobase)-3-oxo-morpholine synthons wherein each of the synthons has a nucleobase that differs from the nucleobase of others of the synthons. The method further includes dividing the resin into portions and treating each of the portions of the amine terminated oligomer on the solid phase synthesis resin with one of the plurality of synthons forming resin bound oligomers having N-[2-(nucleobase)acetyl]-N-(hydroxyethyl) glycyl terminus moiety thereon. The method further includes combining all of the portions of resin together, treating the resin bound oligomers having the hydroxy terminus moieties to convert the hydroxy terminus moieties to amine terminated N-[2-(nucleobase) acetyl]-N-(aminoethyl)glycyl terminus moieties thereby extending the oligomers by one amine terminated peptide nucleic acid unit and repeating further iteration of the method to further extend the oligomer. Upon completion of a product of the desired length, the synthesis is terminated.

In an embodiment of the proceeding process, to fix one or more positions in the oligomeric compound a preselected nucleobase carrying synthon is used during one of said repetitions, after dividing the resin, in place of the plurality of synthon. When so used, this adds the preselected nucleobase synthon to said oligomer in each of the portions of resin and thus fixes that position in the oligomeric compounds. The portions of the resin are not recombined but each is treated separately through further iterations of the method.

In even a further process of the invention there is provided a method of adding peptide nucleic acid units to one of an amine terminated peptide nucleic acid oligomer or an amine terminated amino acid oligomer on a solid phase synthesis resin. The method includes treating the amine terminated oligomer on the solid phase synthesis resin with a 1-(2-carbonylmethylnucleobase)-3-oxo-morpholine synthon forming a resin bound oligomer having a N-[2-(nucleobase) acetyl]-N-(hydroxyethyl)glycyl terminus moiety thereon. The method further includes treating the resin bound oligomer have the hydroxy terminus moiety to convert the hydroxy terminus moiety to an amine terminated N-[2-(nucleobase)acetyl]-N-(amino-ethyl)glycyl terminus moiety and repeating further iteration of the method to further extend the oligomer. Upon completion of a product of the desired length, the synthesis is terminated.

In even a further process of the invention there is provided a method of preparing an oligomeric structure composed of mixed peptide nucleic acid units and amino acid units. The method includes selecting one of an amine terminated peptide nucleic acid structure or an amine terminated amino acid structure on a solid phase synthesis resin and where the structure has at least one peptide nucleic acid unit or at least one amino acid unit. The method further includes treating the amine terminated oligomer on the solid phase synthesis resin with a 1-(2-carbonylmethylnucleobase)-3-oxo-morpholine synthon forming a resin bound oligomer having a N-[2-(nucleobase)acetyl]-N-(hydroxyethyl)glycyl terminus moiety thereon. The method further includes treating the resin bound oligomer have the terminus moiety to convert the terminus moiety to an amine terminated N-[2-(nucleobase) acetyl]-N-(aminoethyl)glycyl terminus moiety. The method further includes effecting one of adding an amino acid monomeric unit to the deprotected amino group of the resin bound extended structure to further extend the structure or repeating further iteration of the method to further extend the structure. Upon completion of a product of the desired length, the synthesis is terminated.

In even a further process of the invention there is provided a method of adding further random peptide nucleic acid units to an amine terminated peptide nucleic acid oligomer on a solid phase synthesis resin. The method includes selecting a plurality of peptide nucleic acid synthons wherein each of the synthons has a nucleobase that differs from the nucleobase of others of the synthons. The method further includes treating the amine terminated unit on the solid phase synthesis resin with the plurality of synthons forming resin bound oligomers having random peptide nucleic acid terminus moieties thereon and repeating further iteration of the method to further extend the oligomer. Upon completion of a product of the desired length, the synthesis is terminated.

In an embodiment of the proceeding process, to fix one or more positions in the oligomeric compound, a preselected nucleobase carrying synthon is used during one of said repetitions in place of the plurality of synthon. When so used, this adds the preselected nucleobase synthon to said oligomer and thus fixes that position in the oligomeric compounds.

In even a further process of the invention there is provided a method of adding further random peptide nucleic acid units to an amine terminated peptide nucleic acid oligomer on a solid phase synthesis resin. The method includes selecting a plurality of peptide nucleic acid monomeric synthons wherein each of the synthons has a nucleobase that differs from the nucleobase of others of the synthons. The method further includes dividing the resin into portions and treating each of the portions of the amine terminated oligomer on the solid phase synthesis resin with one of the plurality of synthons. The method further includes combining all of the portions of resin together and repeating further iteration of the method to further extend the oligomer. Upon completion of a product of the desired length, the synthesis is terminated.

In an embodiment of the proceeding process, to fix one or more positions in the oligomeric compound a preselected nucleobase carrying synthon is used during one of said repetitions, after dividing the resin, in place of the plurality of synthon. When so used, this adds the preselected nucleobase synthon to said oligomer in each of the portions of resin and thus fixes that position in the oligomeric compounds. The portions of the resin are not recombined but each is treated separately through further iterations of the method.

In even a further process of the invention there is provided a method of preparing an oligomeric structure composed of mixed peptide nucleic acid units and amino acid units. The method includes selecting one of an amine terminated peptide nucleic acid structure or an amine terminated amino acid structure on a solid phase synthesis resin and where the structure has at least one peptide nucleic acid unit or at least one amino acid unit. The method further includes treating the amine terminated oligomer on the solid phase synthesis resin with a peptide nucleic acid monomeric synthon forming a resin bound structure having a terminus peptide nucleic acid moiety thereon. The method further includes adding an amino acid monomeric unit to the resin bound structure to extended structure or repeating further iteration of the method to further extend the structure. Upon completion of a product of the desired length, the synthesis is terminated.

In even a further process of the invention there is lo provided a method of preparing an oligomeric structure composed of peptide nucleic acids on a solid phase synthesis resin. The method includes activating a solid phase synthesis resin with an appropriate agent and treating the activated solid phase synthesis resin with a monoprotected diamine synthon to form a resin bound first synthon with a secondary amine and a protected primary amine as an integral part thereof. The method further includes deprotecting the first synthon to form a second synthon having, as an integral part thereof, a secondary amine and a free amine. The method further includes treating the second synthon with a 2-haloacetic acid ester to form a third synthon having, as an integral part thereof, a secondary amine and an acetyl ester. The method further includes treating the third synthon with a 1-haloacetylnucleobase to form a fourth synthon having as an integral part thereof, a covalently bound acetylnucleobase and an acetyl ester thereon. The method further includes deprotecting the fourth synthon to form a fifth synthon having, as an integral part thereof, a free carboxylic acid and a covalently bound acetylnucleobase thereon. The method further includes treating the fifth synthon with a monoprotected ethylenediamine forming an extended first synthon. The method further includes repeating further iteration of the method to further extend the oligomeric structure. Upon completion of a product of the desired length, the synthesis is terminated. The termination of the synthesis can take place before or after deblocking the fourth synthon to give either a protected oligomeric peptide nucleic acid compound or a deprotected oligomeric peptide nucleic acid compound.

Chimeric compounds of the invention include compounds of the structure:

$$[AA]_w-\{[PNA]_u-[AA]_v\}_x-[PNA]_y-[AA]_z$$

wherein each AA, independently, is an amino acid residue; each PNA, independently, is a peptide amino acid residue; u, v, x and y, independently, are 1 to 500; w and z, independently, are 0 to 500; and the sum of u, v, w, x, y and z is less than 500.

In a preferred group of compounds of the invention the sum of u, v, w, x, y and z is less than 100. In an even more preferred groups of compounds of the invention, the sum of u, v, w, x, y and z is less than 25.

Compounds of the invention and compounds prepared by the processes of the invention can be used as inhibitors of various enzymes including phospholipase $A_2$ enzyme. As inhibitors of phospholipase $A_2$, compounds of the invention and compounds prepared by the processes of the invention are useful for the treatment of inflammatory diseases including atopic dermatitis and inflammatory bowel disease.

The compounds of the invention and compounds prepared by the processes of the invention can further be used as gene modulators. Compounds of the invention and compounds prepared by the processes of the invention can further be used in diagnostics since they are capable of specifically hybridizing to nucleic acids of interest in the etiology of diseases. Further the compounds of the invention can be used as research probes and primers especially for the study of enzyme biochemistry and protein-nucleic acid interactions.

BRIEF DESCRIPTION OF THE DRAWINGS

This invention will be better understood when consider in conjunction with the drawings wherein:

FIG. 8 shows a synthesis scheme for the preparation of peptide nucleic acid oligomeric structures utilizing sub-monomer synthons.

DETAILED DESCRIPTION OF THE INVENTION

Figure 1:
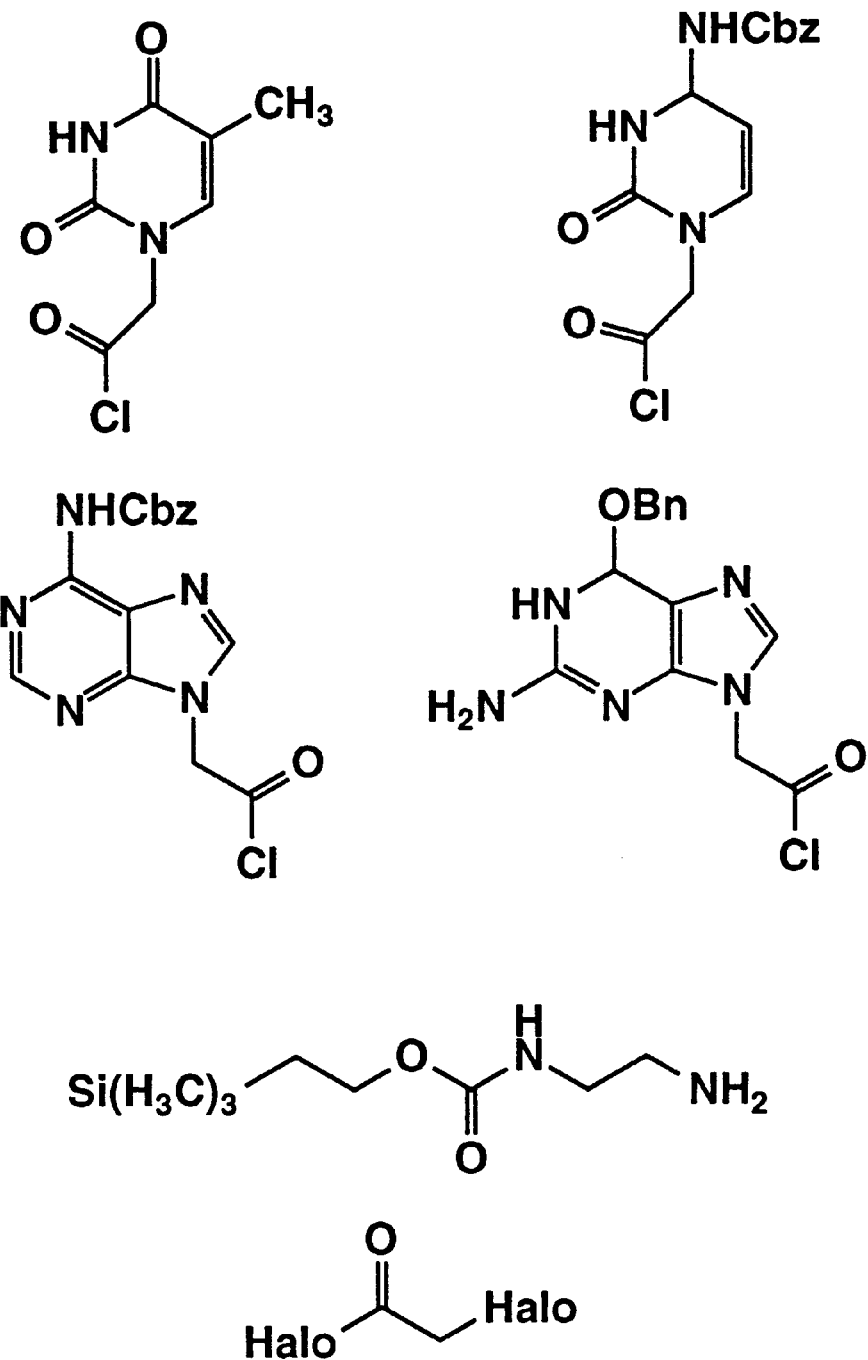
FIG. 1 shows certain sub-monomer peptide nucleic acid synthons utilized in synthetic schemes of the invention.

The synthesis of peptide nucleic acids (also known as PNA) via preformed monomers were f irst described in PCT patent applications WO 92/20702, WO 92/20703, the contents of which are herein incorporated by reference, and further in PCT patent application WO 93/12129, the contents of which are also incorporated by reference. in addition to these patent applications, the synthesis, certain biological properties of and uses of peptide nucleic acids have been published in various journal articles. Two of the most recent of these are Egholm et al., *Nature*, 1993, 365, 566–568 and Patel, D. J., *Nature*, 1993, 365, 490–492. These publication also cited various of the earlier publication directed to peptide nucleic acids.

Peptide nucleic acids have been shown to have higher binding affinities (as determined by their Tm's) for both DNA and RNA than that of DNA or RNA to either DNA or RNA. This increase in binding affinity makes these peptide nucleic acid oligomers especially useful as molecular probes and diagnostic agents for nucleic acid species. Despite these known uses of peptide nucleic acids, it is not known to prepare peptide nucleic acid libraries or to use peptide nucleic acid monomers or sub-monomer in combinatorial techniques.

It has now been found that oligomeric peptide nucleic acids and libraries of peptide nucleic acids can be formed utilizing various combinatorial techniques. Heretofore, it was known only to prepare peptide nucleic acid from preformed complete monomeric units. Further it has now been found that oligomeric peptide nucleic acids, of either pre-determined or random sequences, can be prepared using sub-monomer synthons. Such sub-monomer synthons are especially useful to prepare random sequence peptide nucleic acids and libraries of such random sequence peptide nucleic acids.

Advantageously, in preparing peptide nucleic acid combinatorial libraries, four simple nucleobase building blocks, employed either as fully constructed monomer units or as pre-monomer subunits (sub-monomers), are assembled step-wise to the desired monomer on a resin. Further, chimeric structures can be formed by including additional common amino acid-based building blocks in the libraries.

Libraries of oligomeric PNA or chimeric PNAs are sources of compounds for therapeutic and diagnostic agent development. Further final therapeutic agents can be selected from the library. Thus in one embodiment, this invention embodies libraries comprising either peptide nucleic acids alone or in conjunction with amino acids, as monomer units to create libraries with the ability to bind to biomolecules such as RNA, DNA, or proteins. For binding to nucleic acids, these libraries have the benefit of being able to bind without the charged backbone found in oligonucleotide libraries.

The previous peptide and nucleotide libraries all possess regular backbones with the diversity stemming from the side chains appended to the regular backbone. In a further embodiment of this invention, by incorporating mixtures of amino acids and peptide nucleic acid monomers into the oligomers, chimeric and non-regular backbone libraries can be created. The ability to have a non-regular backbone enhances diversity in a away unattainable in currently known library systems.

In an embodiment of the invention, an amino acid(s) capable of inducing turns, for example proline, are incorporated into the libraries to provide libraries with secondary structure that can be controlled from the current knowledge for peptide turn motifs. Such libraries with an amino acid induced turn are deemed useful for binding to oligonucleotide secondary structures such as stem-loops or hairpins and pseudoknots or duplexes containing a bulged base that induces a helical axis tilt (see Westhof, E., and Jaeger, L., *Curr Opinions Struct. Biol.*, 1992, 2, 327–333 and Ecker, D. J., et al., *Science*, 1992, 257, 958–961).

Thus, in one aspect of the invention, the present invention combines unique peptide nucleic acid monomer units with the standard set of amino acids, in either D or L configurations and/or additional unnatural α or β-amino acids to generate a library. The libraries generated can be used to screen for compounds binding to proteins of interest such as binding to and the inhibition of an enzyme. In addition, these libraries possess the capability to bind at the same time to proteins and to RNA or DNA in close proximity. This has advantages in interfering or enhancing binding of transcription factors or RNA/DNA processing enzymes to their target oligonucleotides or in binding to oligonucleotide secondary structures to stabilize the structure and prevent transcription. The libraries thus contains simple monomers bearing side chains with the potential for interactions of the following types: hydrogen-bond donor and acceptor, ionic, polar, hydrophobic and aromatic.

In one embodiment of the invention, libraries are prepared from known peptide nucleic acid monomers such as those described in the PCT patent applications WO 92/20702, WO 92/20703 and WO 93/12129. Diversity is introduced into these libraries via one of several mechanism. In a first of these, a mixed synthon method is utilized. In this method, a mixture of synthons, like in their chemical reactivity towards a growing oligomer structure but differing as to a functional nucleobase carried thereon, are utilized to added a randomly selected nucleobase carrying synthon on to the growing oligomeric structure. In this manner, libraries of randomly sequenced peptide nucleic acid oligomers are formed. In a further method, diversity is introduced into the libraries via splitting the synthesis resin of a solid support resin, into a number of fraction. Each fraction is then treated with one of the nucleobase carrying synthon to add that synthon to the growing oligomeric structure. After addition, the resin fractions are combined, mixed and further fractionated for the addition of a further nucleobase carrying synthon. In a variation of this method, positions can be "fixed" in the growing oligomeric structure, by reacting the totality of the resin with a single synthon or by reacting each fraction with the same known synthon or with different but known synthons.

In further embodiments of the invention, peptide nucleic acids are synthesized via new synthetic procedures that utilize several sub-monomers that are combined during the synthetic scheme to produce complete peptide nucleic acid units. For the purposes of this invention a sub-monomer is defined as a building blocks that is less than the totality of a complete monomeric unit. Together two or more sub-monomers are combined to give the same structure as would be achieved if a complete monomer were utilized.

The sub-monomer route has various advantages. One such advantage is the fact that certain common sub-monomers that form a part of each monomeric unit of a particular synthetic scheme can be prepared but once in large quantity. Further, less completed synthons bearing the individual nucleobase need to prepared. Further, advantage can be taken of the reactivity of the sub-monomers—that is the sub-monomers are made reactive such that additional coupling agents need not be used to effect growth of the oligomeric structure.

The sub-monomer synthetic process of the invention are useful for not only synthesizing peptide nucleic acids of known or pre-determined sequence but also for the synthesis of random sequence peptide nucleic acids and libraries of such randomly synthesized peptide nucleic acids. This is particularly useful for certain combinatorial screening techniques.

A key feature of combinatorial techniques is that thousands of molecules can be screened in a small number of assays. To detect an active sequence generated via a combinatorial technique, the concentration of the active molecule is selected to be sufficiently great such that the molecule can be detected within the sensitivity of the chosen assay. As will be recognized, the number of unique oligomer sequences within a subset produced via a combinatorial technique depends on the length of the oligomer and the number of different monomers employed. The number of sequences can be determined by raising the number of monomers to a power equal to the number of random positions. This is illustrated in Table I. Table I also indicates the concentration of each sequence when the subset concentration is 100 μM, a typical high-test concentration. It has been found that the number of monomers and their length can be based upon an estimate of the expected $IC_{50}$ (i.e., a concentration at which 50% of enzyme activity is inhibited) that is desirable in a final oligomeric compound. For an expected $IC_{50}$ of 100 nM, the complexities shown in Table I are acceptable, that is, the libraries shown in Table I have complexities that would allow detection of a unique sequence with an $IC_{50}$ of about 100 nM or less.

TABLE I

Complexity of Libraries

| Length | SequencesnM Each Sequence Per SubsetAt 100 μM Subset |
|---|---|
| 5 Monomers | |
| 4-mer | 125800 |
| 5-mer | 625160 |
| 6 Monomers | |
| 4-mer | 216463 |
| 5-mer | 1,29677 |
| 7 Monomers | |
| 4-mer | 343291 |
| 8 Monomers | |
| 4-mer | 512195 |
| 10 Monomers | |
| 4-mer | 1,000100 |

If five monomers are selected for a library, then the library will have a length of five monomer units, XNNNN, where N is an equal molar mixture of monomer units and X is a different monomer unit in each of the five subsets. For ease in synthesis, the fixed position can be selected as the right end of the molecule. After assay for inhibition of $PLA_2$ activity as described below, position X is fixed with the residue giving the greatest inhibition and the next subset is synthesized and screened. The fixed position then shifts towards the left end of the oligomer as unrandomization proceeds. Five rounds of synthesis and screening are required to determine a unique inhibitor.

The monomer design of the invention, achieved via either a full monomer or via sub-monomers, allows for the combination of rational drug design with a screen of thousands of compounds. One such screen wherein libraries of peptide nucleic acids oligomer and chimeric peptide nucleic acidpeptides, is a screen for activity against $PLA_2$.

Elevated levels of type II $PLA_2$ are correlated with a number of human inflammatory diseases. Phospholipases $A_2$ ($PLA_2$) are a family of enzymes that hydrolyze the sn-2 ester linkage of membrane phospholipids resulting in release of a free fatty acid and a lysophospholipid [see Dennis, E. A., *The Enzymes*, 1983, ed. Boyer, P. D. (Academic Press, New York), Vol. 16, pp. 307–353]. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to plateletactivating factor. $PLA_2$ is regulated by pro-inflammatory cytokines and thus occupies a central position in the inflammatory cascade (see Dennis, ibid.; Glaser, K. B., Mobilio, D., Chang, J. Y. & Senko, N., *TiPs Reviews*, 1992, 14, 92–98; and Pruzanski, W., Scott, K., Smith, G., Rajkovic, I., Stefanski, E. & Vadas, P., *Inflammation* 1992, 16, 451–457).

All mammalian tissues evaluated thus far have exhibited $PLA_2$ activity. At least three different types of $PLA_2$ are found in humans: pancreatic (type I), synovial fluid (type II) and cytosolic. Other studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath, B. S., Fawzy, A. A. & Franson, R. C., *Inflammation* 1988, 12, 549–561) or into the articular space of rabbits (Bomalaski, J. S., Lawton, P. & Browning, J. L., *J. Immunol.* 1991, 146, 3904–3910) produced an inflammatory response. When the protein was denatured before injection, no inflammatory response was produced.

The type II $PLA_2$ enzyme from synovial fluid is small (about 14 kD) and distinguished from the type I enzymes (e.g. pancreatic) by sequence and the pattern of disulfide bonds present—both types require calcium for activity (Dennis, ibid.). The crystal structures of secreted $PLA_2$ enzymes from venom and pancreatic $PLA_2$ with and without inhibitors have been reported (Scott, D. L., White, S. P., Otwinowski, Z., Yuan, W., Gelb, M. H. & Sigler, P. B., *Science*, 1990, 250, 1541–1546). Recently the crystal structure of $PLA_2$ from human synovial fluid has been solved (Wery, J.-P., et al., *Nature*, 1991, 352, 79–82). The structures establish the role of the active site calcium and the amino acid residues involved in catalysis. The calcium acts as a Lewis acid to activate the scissile ester carbonyl and bind the lipid, and a His-Asp side chain dyad acts as general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged aminoterminal helix is situated above the opening of the hydrophobic cleft. Several lines of evidence suggest that the N-terminal portion is the interfacial binding site (Achari, A., Scott, D., Barlow, P., Vidal, J. C., Otwinowski, Z., Brunie, S. & Sigler, P. B., *Cold Spring Harbor Symp. Quant. Biol.*, 1987, 52, 441–452; Cho, W., Tomasselli, A. G., Heinrikson, R. L. & Kezdy, F. J., *J. Biol. Chem.*, 1988, 263, 11237–11241; Yang, C.-C. & Chang, L.-S., *Biochem. J.*, 1989, 262, 855–860: and Noel, J. P., Deng, T., Hamilton, K. J. & Tsai, M.-D., *J. Am. Chem. Soc.*, 1990, 112, 3704–3706).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. The evidence favoring this hypothesis comes from studies revealing that rapid changes in $PLA_2$ activity occur concurrently with changes in the fluorescence of a membrane probe (Burack, W. R., Yuan, Q. & Biltonen, R. L., *Biochemistry*, 1993, 32, 583–589). This suggests that lipid rearrangement is occurring during the interfacial activation process. $PLAN_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region.

Fluorescence microscopy was used to simultaneously identify the physical state of the lipid and the position of the enzyme during catalysis (Grainger, E. W., Reichert, A., Ringsdorf, H. & Salesse, C., *FEBS Lett.*, 1989, 252, 73–82). These studies clearly show that $PLA_2$ binds exclusively at the boundary region between liquid and solid phase lipid.

While the hydrolysis of the secondary ester bond of 1, 2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate (Dennis, ibid.; Achari, ibid.). As a result, competitive inhibitors of $PLA_2$ either have a high affinity for the active site of the enzyme before it binds to the substrate bilayer or partition into the membrane and compete for the active site with the phospholipid substrate. Although a number of inhibitors have been described that show promising inhibition of $PLA_2$ in biochemical assays (Yuan, W., Berman, R. J. & Gelb, M. H., *J. Am. Chem. Soc.*, 1987, 109, 8071–8081; Lombardo, D. & Dennis, E. A., *J. Biol. Chem.*, 1985, 260, 7234–7240; Washburn, W. N. & Dennis, E. A., *J. Biol. Chem.*, 1991, 266, 5042–5048; Campbell, M. M., Long-Fox, J., Osguthorpe, D. J., Sainsbury, M. & Sessions, R. B., *J. Chem. Soc., Chem. Commun.*, 1988, 1560–1562; and Davidson, F. F., Hajdu, J. & Dennis, E. A., *Biochem. Biophys. Res. Commun.*, 986, 137, 587–592), reports describing in viva activity are limited (Miyake, A., Yamamoto, H., Takebayashi, Y., Imai, H. & Honda, K., *J. Pharmacol. Exp. Ther.*, 1992, 263, 1302–1307).

For the purposes of this specification, a sulfonyl moiety is defined to include both aryl and alkyl radicals. Thus sulfonyl includes tosylates, brosylates, nosylates, mesylates, triflates, nonaflates and tresylates. Further for the purposes of this specification halo and halide moieties include the halogens F, Cl, Br or I. Additionally for the purposes of this specification an acetyl radical is considered to be inclusive of not only an unsubstituted $CH_3C=O$ moiety but also a substituted form thereof wherein one of the methyl hydrogen atoms is removed (forming a methylene carbonyl moiety) and is replaced with the substituent. Example of such usage include the structure $BrCH_2C(=O)Cl$ named as bromoacetyl chloride, where the chloro group is now the substituent that replaced the extracted hydrogen atom and the radical [(thymine)$CH_2C(=O)$] named as [(thymin-1-yl) acetyl] wherein the thymine nucleobase replaces the extracted hydrogen atom.

Solid phase amino acid synthesis resin suitable for use with the invention include resins such as hydroxymethyl polystyrene, PAM, Tentagel, Wang or MBHA. Such resins can be utilized in both batch wise synthesis or via machine synthesis. In practicing batch wise synthesis, for facilitating removal of residual reactants from polystyrene resin, after completion of a reaction step, the resin is washed and dried to remove all solvent. The resin is then re-swollen for the next procedure. Machine synthetic techniques are those known in the arts of peptide synthesis.

One preferred sub-monomer synthon of the invention is a bifunctional acetyl synthon having a halide functional group and one of either an alkyl halide or sulfonyl functional group. Thus such preferred bifunctional acetyl synthons include haloacetyl halide or sulfonylacetyl halide synthons. A particular preferred groups of such synthons include tosyl acetyl halide, mesyl acetyl halide, brosyl acetyl halide, nosyl acetyl halide, triflyl acetyl halide, nonaflyl acetyl halide or tresyl acetyl halide synthons as well as chloroacetyl chloride, chloroacetyl bromide, bromoacetyl chloride, bromoacetyl bromide, iodoacetyl chloride, iodoacetyl bromide, fluoro acetylchloride and fluoro acetylbromide.

For certain of the sub-monomer synthetic synthesis of the invention, preferred amine protecting groups include tetramethyl-1,2-disilylethylene and trimethylsilylethoxycarbonyl both of which can be removed with fluoride ion. Other amine protecting groups for use in the invention include t-butyloxycarbonyl removable with trifluoroacetic acid in $CH_2Cl_2$, DMF or equivalent solvent; fluorenylmethyloxycarbonyl removable with piperidine in DMF; or triphenylmethyl or one of the possible methoxysubstituted triphenymethyl protecting groups, removable with trichloroacetic acid in dichloromethane or the like.

For reaction of the certain sub-monomer synthons of the invention or certain bifunctional acetyl synthons of the invention with support resin or growing oligomer, the concurrent use of an acid scavenger is preferred. Such acid scavengers include tertiary alkyl amines such as triethylamine and related trialkyl amine compounds including but not limited to diisopropylethylamine, dicyclohexylethylamine, dicyclohexylmethylamine, 1,2,2,6,6-pentamethyl piperidine and N-methyl morpholine.

Figure 2A:
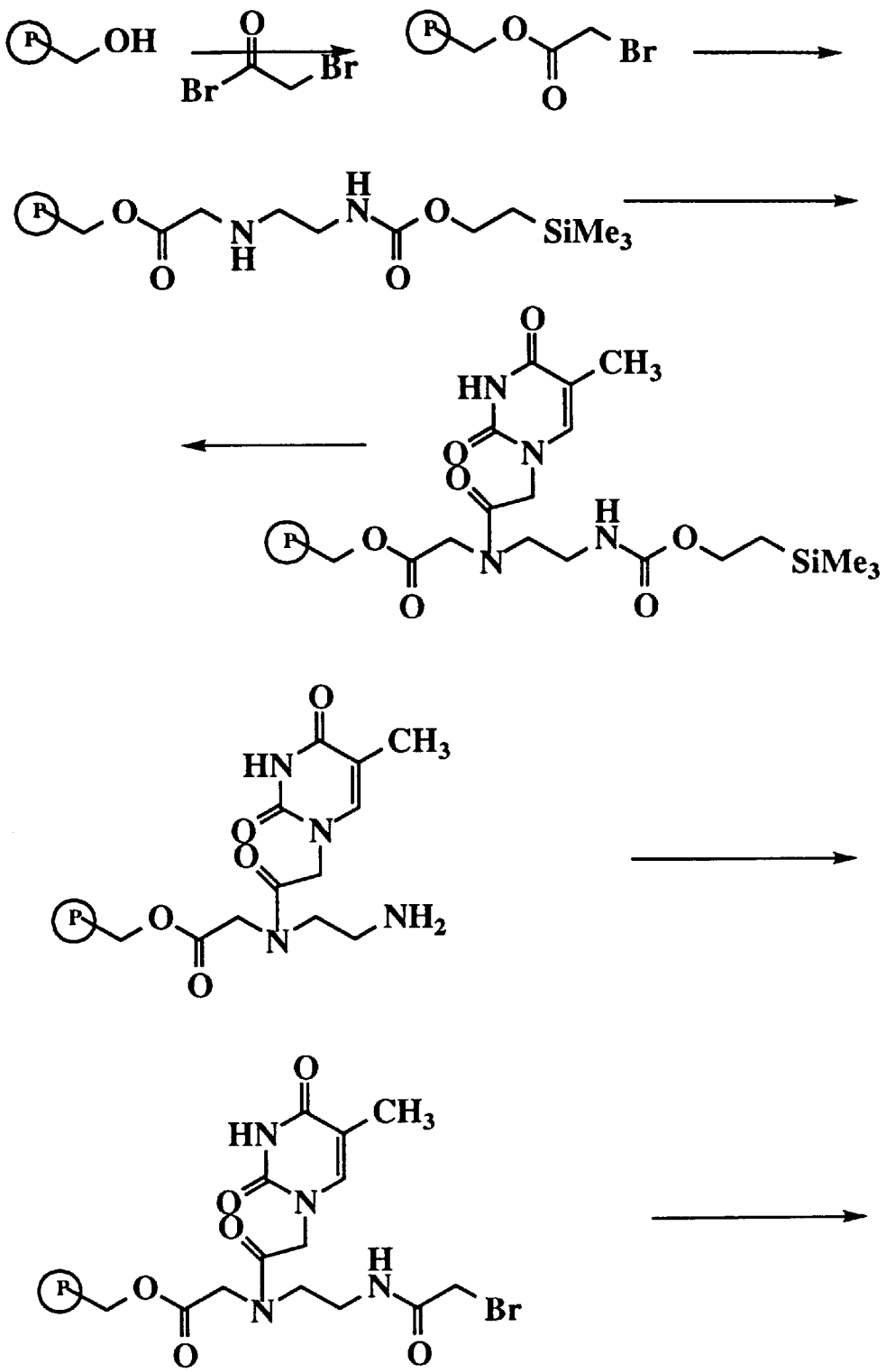
FIG. 2 shows a synthesis scheme for the preparation of peptide nucleic acid oligomeric structures utilizing the sub-monomer synthons of FIG. 1.
Figure 2B:
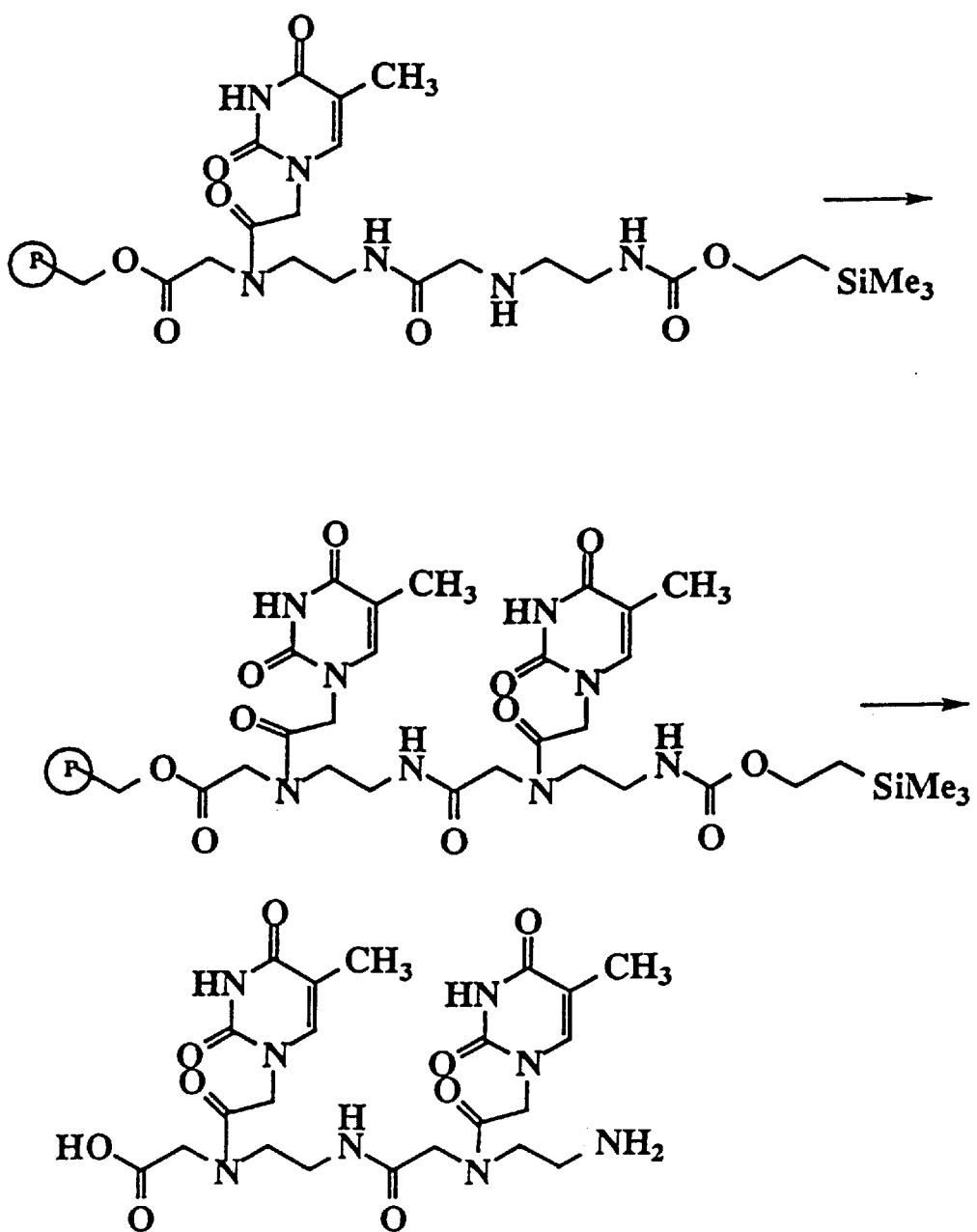

FIG. 2 illustrates a synthetic scheme for the preparation of peptide nucleic acids of predesigned sequence or peptide nucleic acid combinatorial libraries of any desired length utilizing certain sub-monomer building blocks or synthons as are shown in FIG. 1. One of the synthons is a synthon carrying one of the individual nucleobases. In effecting the synthesis illustrated in FIG. 2, the synthons utilized for this synthesis can be characterized as an acetylnucleobase fragment, e.g. 2-(nucleobase)acetyl chloride; an ethylenediamine fragment, e.g. N-(2-trimethysilylethoxycarbonyl)-1, 2-diaminoethane or N-Fmoc-1,2-diaminoethane) hydrochloride; and an haloacetyl halide or sulfonylacetyl halide fragment (where halo, halide and sulfonyl are as define previously), e.g. bromoacetyl chloride. In the synthesis of either known sequence peptide nucleic acids or peptide nucleic acid combinatorial libraries, the assembly of the desired peptide nucleic acid oligomer libraries is carried out, as for instance, by attaching a bromoacetyl chloride or mesylacetyl chloride synthon to a solid phase amino acid synthesis resin such as hydroxymethyl polystyrene, PAM, Tentagel, or Wang. After attachment, the resin bound acetyl chloride synthon is reacted with the ethylenediamine synthon in the presence of an acid scavenger to displace the 2-halo element, i.e. the 2-bromo element, of the original bromoacetyl fragment. The unprotected secondary amine of the ethylene diamine portion of this resulting fragment is next reacted with a 1-haloacetylnucleobase synthon, if a fixed position is desired, and, if a randomized position is desired, in one embodiment of the invention with a mixture of the desired substituted halo acetyl synthons. In a further embodiment of the invention, the resin can be split into portion and each portion reacted with a different 1-haloacetylnucleobase synthon. For each of these, the 1-haloacetylnucleobase or 1-haloacetylnucleobases are added in the presence of an acid scavenger. Particularly suitable as the acid scavenger is a hindered tertiary amine base; however, other acid scavengers can also be used. If the resin is split, it can be recombined. Next fluoride ion is used to deprotect the terminal amine of the ethylene diamine fragment. At this point in the synthesis a first peptide nucleic acid unit has been synthesized on the resin.

Formation of the second peptide nucleic acid unit is effected by reacting the terminal amine of the first peptide nucleic acid unit with further haloacetyl halide or sulfonylacetyl halide synthon, again in the presence of an acid scavenger, to create the glycine portion of the second peptide nucleic acid unit now attached to the first peptide nucleic acid unit. This glycine moiety is now reacted with the ethylenediamine synthon, again in the presence of an acid scavenger, to add the ethylamine portion of the second peptide nucleic acid unit to the growing peptide nucleic acid oligomer. This is followed by reacting the unprotected secondary amine of the second ethylene diamine fragment with a second haloacetylnucleobase synthon, if a fixed position is desired, and, if a randomized position is desired, a mixture of the desired nucleobase substituted halo acetyl synthons or splitting of the resin into portions as described above. Either the single base or the mixture of bases are added in the presence of an acid scavenger. If the resin has been split, it can be re-combined. Next fluoride ion is used to deprotect the terminal amine of the second PNA unit ethylene diamine moiety.

A third peptide nucleic acid unit is then added in the same manner by again reacting the terminal amine with a further haloacetyl halide or sulfonylacetyl halide synthon as before in the presence of a hindered tertiary amine base. The process is repeated as many times as is necessary to prepare the desired fully protected, resin-attached peptide nucleic acid library with the desired number of fixed and randomized positions. The completed peptide nucleic acid can then be deprotected and cleaved from the resin or cleaved first from the resin and then deprotected. Alternately, for a library of randomly generated peptide nucleic acids, the blocked peptide nucleic acids could remain on the resin and treated with an appropriate biological testing medium to assay for activity.

Variations possible using this method include the use of alternate (substituted) haloacetyl units, such as α-methyl or α-protected hydroxymethyl haloacetyl halide at any position in the oligomer desired. Substitutions or chain length variation in the diaminoethane synthon are also possible and substitution on the acetyl synthon are also considered within the scope of the invention. Variations also include the use of alternate synthons, where any substituent desired to provide binding motifs such as charge, hydrogen bond accepting or donating properties, or hydrophobic and aromatic pi-interactions at any position in the oligomer desired. Substitutions or chain length variation in the synthons are also possible and substitution on the acetyl portion are also with the scope of this method of the invention.

The repeating nature of the synthetic sequence of FIG. 2 can be interrupted at anytime there is a free terminal amine present and an amino acid can be introduced by standard peptide coupling techniques, either as a single fixed amino acid residue or a mixture of amino acids to provide a random position before continuing as described above to the desired length oligomer. This synthetic sequence can also be utilized to extend a normal peptide with peptide nucleic acid units.

Figure 3:
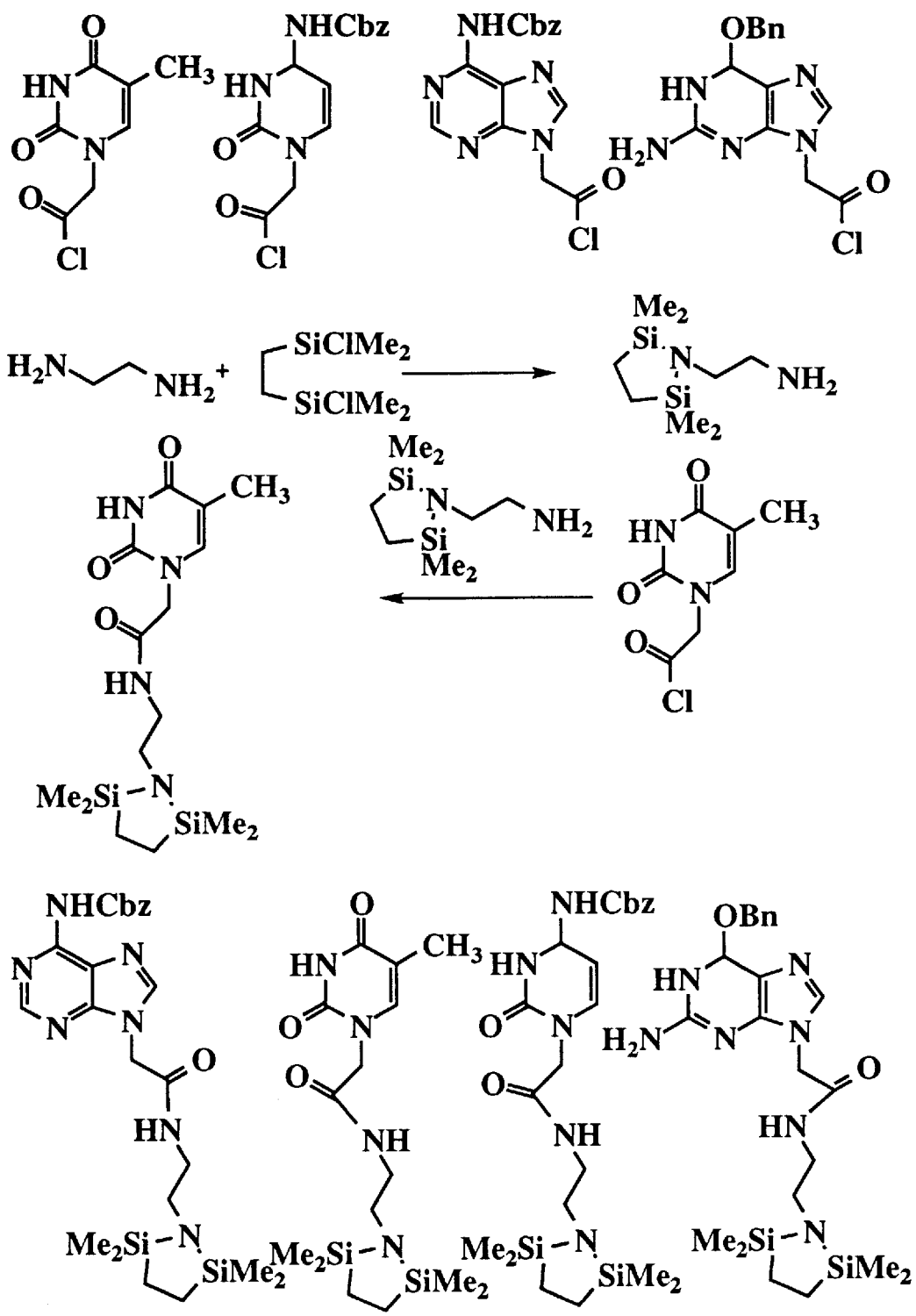
FIG. 3 shows a synthesis scheme for the preparation of further sub-monomer peptide nucleic acid synthons.
Figure 4:
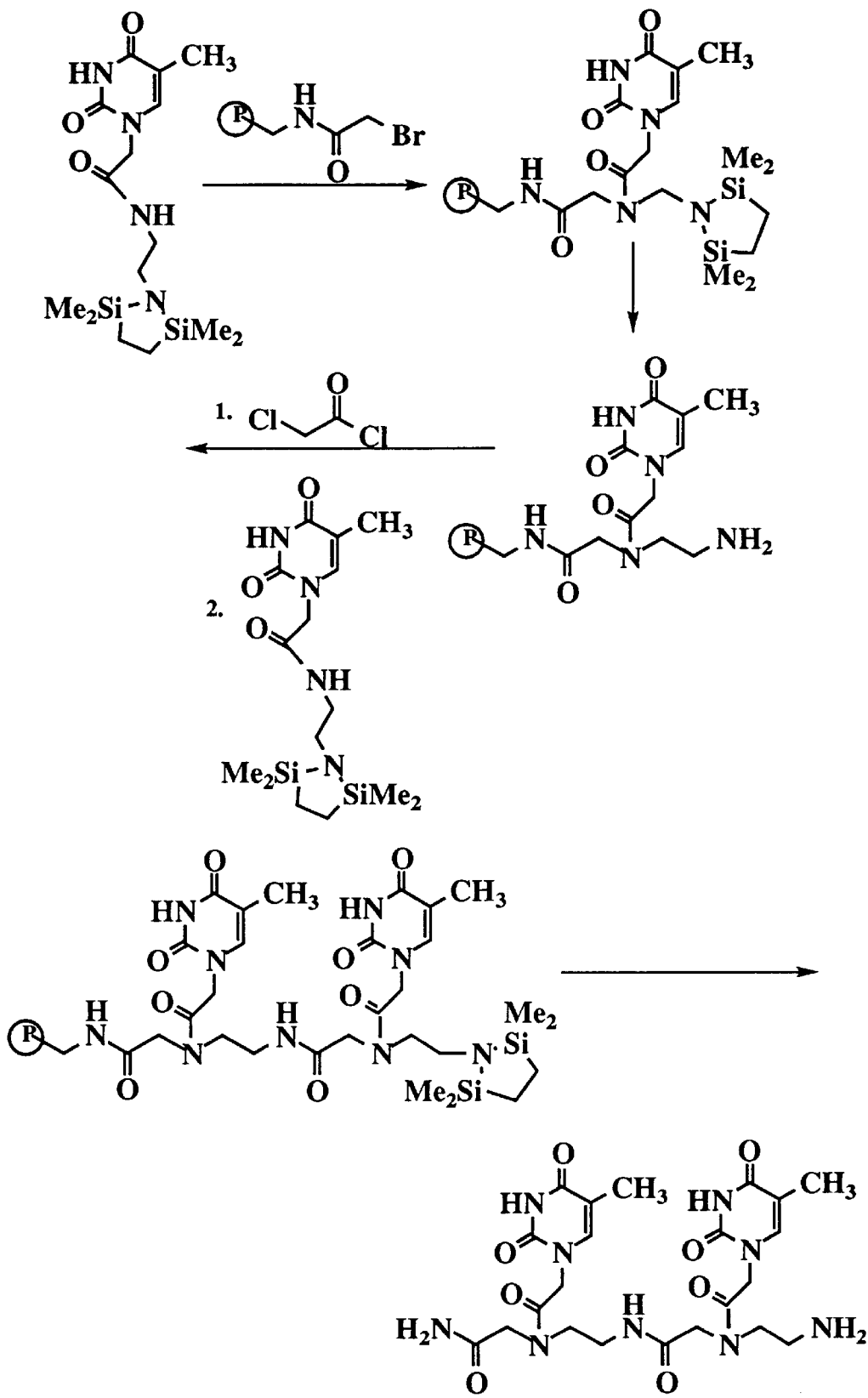
FIG. 4 shows a synthesis scheme for the preparation of peptide nucleic acid oligomeric structures utilizing the sub-monomer synthons of FIG. 3.

In a second method for the preparation of peptide nucleic acids of a predesigned sequence or a peptide nucleic acid combinatorial libraries of any desired length illustrated in FIG. 4, further sub-monomer building blocks or synthons are assembled. These sub-monomer are illustrated in FIG. 3. In utilizing this method, the construction of a peptide nucleic acid of predetermined sequence or a peptide nucleic acid combinatorial library of any desired length is effected by treating a resin (or a preexisting peptide nucleic acid or amino acid unit on a resin) with an acetyl synthon that has two active functional groups thereon to add the acetyl synthon to the resin (or existing peptide nucleic acid or amino acid unit). This is then treated with an ethylenediamine-acetyl-nucleobase synthon wherein one of the amino groups of the diamine is present in a blocked or protected form, e.g. 2-(tetramethyl-1,2-disilylethylene)-1-[(2-nucleobase)acetyl]-ethylenediamine, if a fixed position is desired, and employing a mixture of such synthons (or split portions of the resin, as described for the previous method), if a randomized position is desired.

As is illustrated in FIG. 4, the assembly of the desired peptide nucleic acid oligomers libraries is carried out by attaching a 2-(tetramethyl-1,2-disilylethylene)-1-[2-(nucleobase)acetyl] ethylenediamine synthon to a solid phase amino acid synthesis resin having an haloacetylated amine function such as MHBA or an aminoacid loaded resin. Next the blocking or protecting group on the terminal amine (of the ethylenediamine fragment of the second synthon) is deprotected. For the above tetramethyl-1,2-disilylethylene blocking group, fluoride ion is utilized to deprotect the terminal amine of the ethylenediamine fragment. This completes the synthesis of one complete peptide nucleic acid unit on the resin or the addition of a further peptide nucleic acid unit to a preexisting peptide nucleic unit or peptide nucleic acid oligomer.

The addition of the second peptide nucleic acid unit is then effected by reacting the above product (still on the resin) with bifunctional acetyl synthon, e.g. a haloacetyl halide fragment. This is then treated a second 2-(tetramethyl-1,2-disilylethylene)-1-[2-(nucleobase) acetyl] ethylenediamine synthon followed by deprotection. Such deprotection is again effected using fluoride ion if a tetramethyl-1,2-disilylethylene protecting group is utilized. As before, this deprotects the terminal amine of the ethylenediamine fragment.

The third peptide nucleic acid unit is then added by again reacting the existing oligomer on the resin with a haloacetyl halide fragment followed by treating with a third 2-(tetramethyl-1,2-disilylethylene)-1-[2-(nucleobase) acetyl]-ethylenediamine synthon. This process is repeated through as many iterations as is necessary to prepare the desired fully protected, resin-attached peptide nucleic acid or peptide nucleic acid library. The completed peptide nucleic acid or library can then be deprotected and cleaved from the resin or cleaved first from the resin and then deprotected.

Variations possible under this second synthetic method of the invention include the use of alternate 2-(tetramethyl-1, 2-disilylethylene)-1-[2-(nucleobase)acetyl] ethylenediamine synthons, where any substituent desired to provide binding motifs such as charge, hydrogen bond accepting or donating properties, or hydrophobic and aromatic pi-interactions at any position in the oligomer desired. Substitutions or chain length variation in the diaminoethane unit are also possible and substitution on the acetyl portion are also with the scope of this method of the invention. The repeating nature of this synthetic sequence can be interrupted at anytime there is a free terminal amine present and an amino acid can be introduced by standard peptide coupling techniques, either as a single fixed amino acid residue or a mixture of amino acids to provide a random position before continuing as described above to the desired length oligomer. The synthetic sequence can also be utilized to extend a normal peptide with peptide nucleic acid units.

Figure 5:
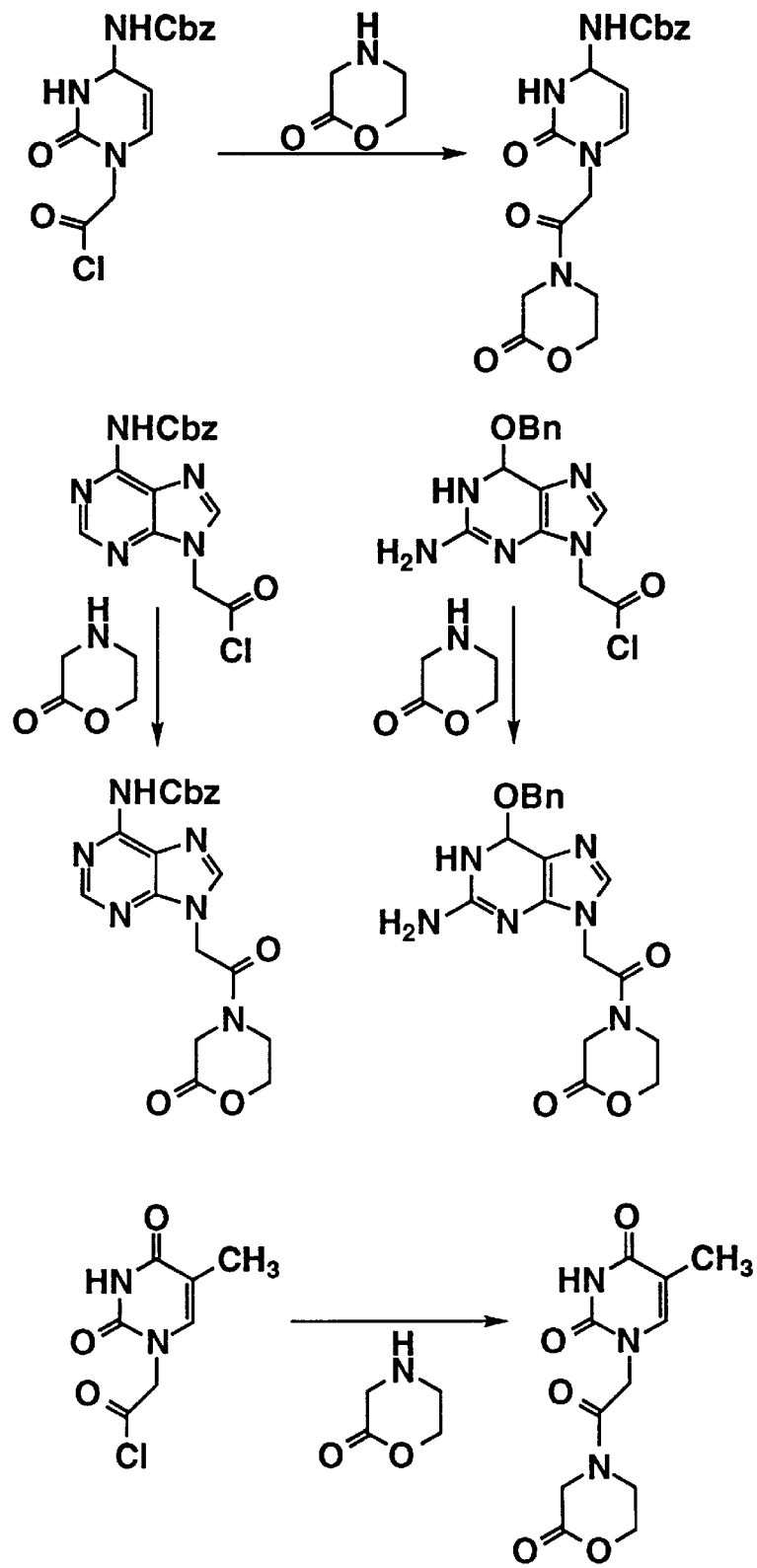
FIG. 5 shows a synthesis scheme for the preparation of further sub-monomer peptide nucleic acid synthons.
Figure 6:
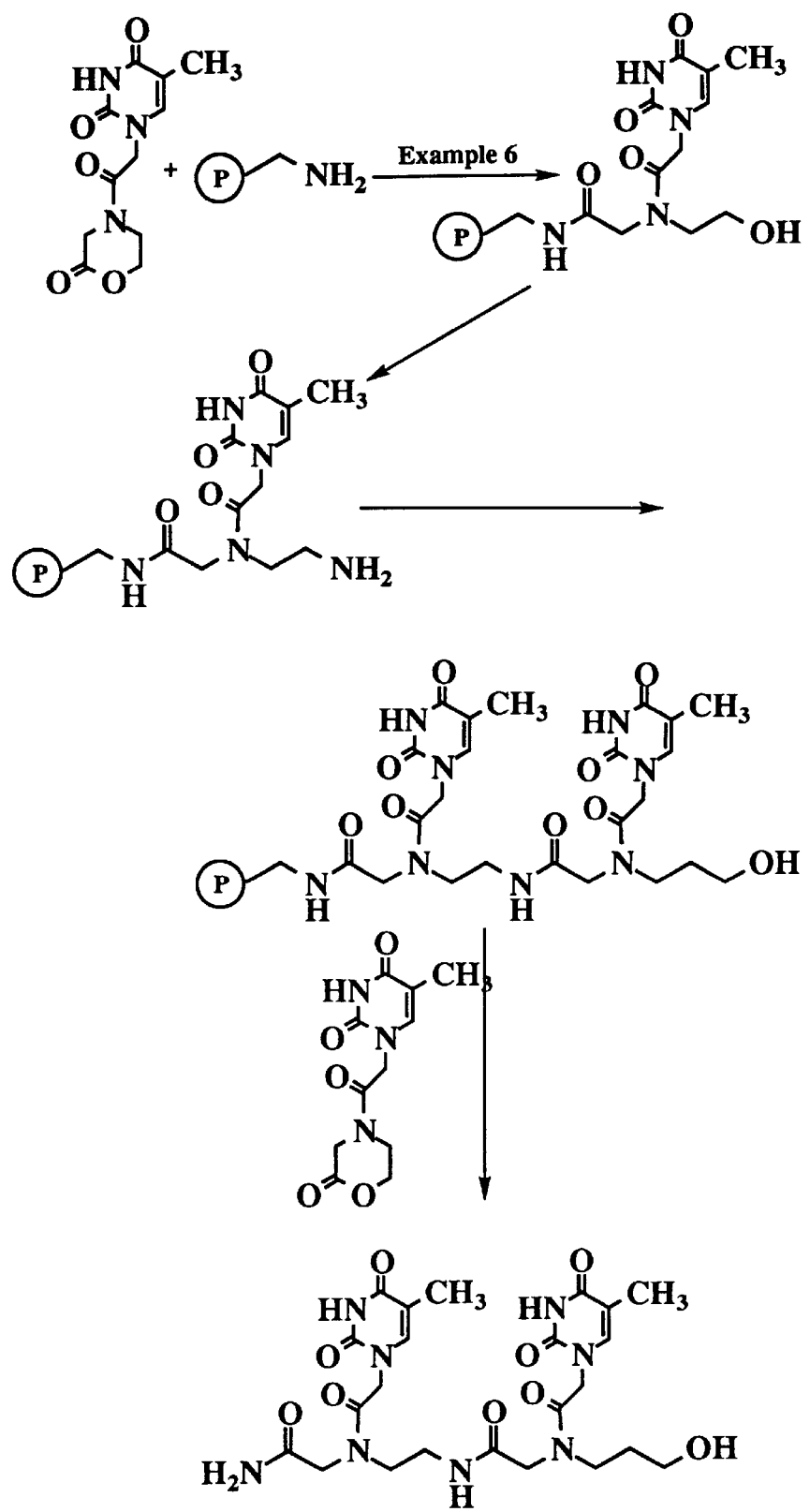
FIG. 6 shows a synthesis scheme for the preparation of peptide nucleic acid oligomeric structures utilizing the sub-monomer synthons of FIG. 5.
Figure 7:
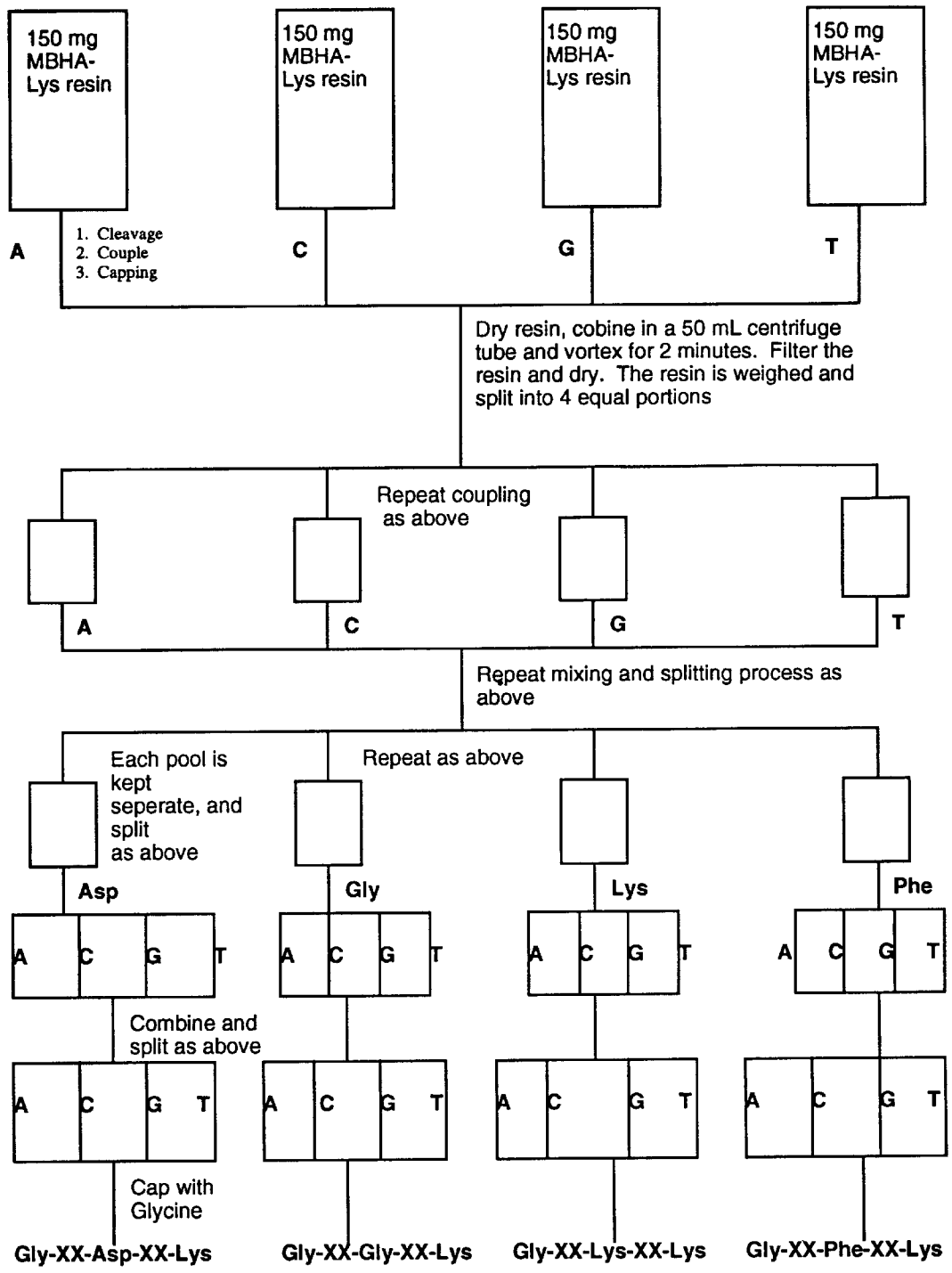
FIG. 7 shows one logic flow scheme for the preparation of a chimeric oligomeric structure of the form Gly-XX-Y-XX-Lys wherein each X is a peptide nucleic acid and each Y is an amino acid in accordance with preferred embodiments.

In a further method for the preparation of peptide nucleic acids of a predesigned sequence or a peptide nucleic acid combinatorial libraries of any desired length is illustrated in FIG. 6. This method utilizes further submonomer building blocks or synthons as illustrated in FIG. 5. Utilizing this method, the construction of a peptide nucleic acid of predetermined sequence or a peptide nucleic acid combinatorial library of any desired length is effected by treating an amine terminated resin (or an amine terminated preexisting peptide nucleic acid or amino acid unit on a resin) with a oxo-morpholine synthon that includes a nucleobase thereon. Suitable for use as this synthon is a 1-[2-(nucleobase) carbonylmethyl]-3-oxo-morpholine synthon, e.g. 1-[2-(thymin-1-yl) carbonylmethyl]-3-oxo-morpholine, 1-{2-[$N^4$-(benzyloxycarbonyl) cytosin-1-yl]carbonylmethyl}-3-oxo-morpholine, 1-{2-[$N^2$-(benzyloxycarbonyl)-$N^6$-(benzyloxy)-2-aminopurin-9-yl]carbonylmethyl}-3-oxo-morpholine or 1-{2-[$N^6$-(benzyloxycarbonyl) adenin-9-yl] carbonylmethyl}-3-oxo-morpholine. In this method, the assembly of the desired peptide nucleic acid oligomers is carried out by attaching a 1-[2-(nucleobase) carbonylmethyl]-3-oxo-morpholine synthon to a solid phase amino acid synthesis resin having an amine function such as MHBA or a peptide nucleic acid or an amino acid loaded resin. The resin is reacted with the synthon by treating the resin with the 1-[2-(nucleobase) carbonylmethyl]-3-oxo-morpholine synthon to added a modified peptide nucleic acid unit. The modified peptide nucleic acid unit is a unit that is terminated with a hydroxyl functionality versus an amine functionality of a normal peptide nucleic acid unit. The terminal modified peptide nucleic acid unit is then converted to a normal peptide nucleic acid unit by conversion of the terminal hydroxyl group to an amine group. This can be effected by an method compatible with the remainder of the oligomer and resin. A particularly preferred method is via a Mitsunobu reaction. Thus the resulting unprotected alcohol fragment, located on the resin having a single unit or a growing oligomer thereon, is treated with diethylazodicarboxylate, triphenylphosphine and bis(t-butoxycarbonyl)imide or with dipheylphosphoryl azide coupled with reduction to convert the hydroxyl group to an amine group followed by removing the t-BOC group with trifluoroacetic acid. In doing so, this converts the just added unit to a normal peptide nucleic acid unit.

A second peptide nucleic acid unit is then added via the same set of reactions, namely, reacting the existing peptide nucleic acid unit or peptide nucleic acid oligomer on the resin with a second 1-[2-(nucleobase) carbonylmethyl]-3-oxo-morpholine synthon followed by conversion of the resulting unprotected alcohol group with diethylazodicarboxylate, triphenylphosphine, and bis (t-butoxycarbonyl) imide to an amine followed by removing the t-BOC group with trifluoroacetic acid. This process is repeated through as many iterations as is necessary to prepare the desired fully protected, resin-attached peptide nucleic acid or peptide nucleic acid library. The completed peptide nucleic acid or library can then be deprotected and cleaved from the resin or cleaved first from the resin and then deprotected. Variations possible under this invention are the use of alternate (substituted) morpholine synthons, such as methyl or protected hydroxymethyl at any position in the oligomer desired. Use of non-natural nucleobases and substitution on the acetyl portion are also within the scope of the invention.

In a fourth method for preparing random peptide nucleic acid oligomeric compounds, peptide nucleic acid monomer units are linked to form an oligomer using a modification of method for synthesizing peptides on solid supports as pioneered by Merrifield. In practicing this method, in combination with a SURF selection technique, an equimolar or essentially equimolar incorporation of each monomer at each randomized position is desired. Since the coupling rates of the monomers may vary, in one embodiment, monomers are coupled separately to a portion of the solid support as follows:

1) A solid support, usually 1–10% crosslinked polystyrene or polyethylene glycol grafted polystyrene, is separated into portions (of number equal to the number of monomers in the library) of equal weight. Each of these is reacted with one of the desired N-amino and side chain protected free carboxylic acid peptide nucleic acid or peptide nucleic acid-like monomers using hydroxybenzotriazole and a carbodiimide coupling agent or one of the numerous uronium salts. The N-terminal amino protecting group is cleaved using trifluoroacetic acid in $CH_2Cl_2$, DMF or equivalent solvent to generate a new terminal amino functionality, if the protecting group is a t-butyloxycarbonyl, or piperidine in DMF, if the protecting group is a fluorenylmethyloxycarbonyl, or trichloroacetic acid in dichloromethane or the like if the protecting group is a triphenylmethyl or one of the possible methoxysubstituted triphenymethyl protecting groups at the end of the extended oligomer. The extent of the coupling reaction is optimized to be $\geq 90\%$ completed by varying the monomer and coupling agent concentrations and total equivalents and the coupling time. After a coupling, the support is mixed thoroughly, then divided equally and monomers are again reacted individually to a portion of the support. This cycle is repeated for each random position until desired a "fixed" position is reached.

2) At "fixed" positions of the oligomer, each monomer is reacted individually to a portion of the support, but the portions are not mixed. Instead each subset is further divided into the number of portions corresponding to the number of monomers. Each portion of support is then reacted with a different monomer, followed by mixing as above. Repeating this cycle for each of the different subsets of supports results in randomization in positions following the fixed position in the sequence. The resulting subsets are unique only in the fixed position.

3) Once the oligomer synthesis is complete, oligomers are cleaved from the solid support and side chain protecting groups are removed by incubation for 1–2 h at room temperature in an appropriate deprotection mixture such as trifluoroacetic acid/trifluoromethanesulfonic acid containing cresol and arylmethyl sulfide as cation scavengers. The supernatant containing the oligomer is then removed from the spent resin. The oligomer is desalted and protecting groups byproducts removed by HPLC or size exclusion chromatography.

In a fifth method for preparing random peptide nucleic acid oligomeric compounds, peptide nucleic acid monomer units are linked to form an oligomer using a modification of methods for synthesizing peptides on solid supports as pioneered by Merrifield. In practicing this method, in combination with a SURF selection technique, an equimolar or essentially equimolar incorporation of each monomer at each randomized position is desired. Since the coupling rates of the monomers may vary, in this embodiment, the coupling rates of the monomers to each other are determined and monomers concentrations are adjusted—based on the determined coupling rates—so that the relative coupling rate of each monomer in the mixture of incoming monomer (activated form) is the same. The coupling mixture is reacted with the resin/solid support at each step in the oligomer synthesis where a random position is desired as follows:

1) A solid support, usually 1–10% crosslinked polystyrene or polyethylene glycol grafted polystyrene, is reacted with the mixture of incoming monomer, with adjusted concentrations of the desired N-amino and side chain protected free carboxylic acid peptide nucleic acid or peptide nucleic acid-like monomers using hydroxybenzotriazole, and a carbodiimide coupling agent or one of the numerous uronium salts. The N-terminal amino protecting groups are cleaved using trifluoroacetic acid in $CH_2Cl_2$ or DMF or some similar solvent to generate a new terminal amino functionality, if the protecting group is a t-butyloxycarbonyl and piperidine in DMF if the protecting group is a fluorenylmethyloxycarbonyl or trichloroacetic acid in dichloromethane or the like if the protecting group is a triphenylmethyl or one of the possible methoxysubstituted triphenymethyl protecting groups at the end of the extended oligomer. The extent of the coupling reaction is optimized to be $\geq 90\%$ completed by varying the monomer and coupling agent concentrations and total equivalents and the coupling time. After a coupling, the support is washed free of residues, the terminal deprotection reaction and coupling cycle is repeated for each random position until the "fixed" position is reached.

2) At any "fixed" position of the oligomer, each monomer is reacted individually to a portion of the support. The portions used equals the number of monomers to be used to fix the desired subsets. After this the subsets are not mixed. Instead each subset is further deprotected and reacted with the adjusted activated monomer mixture. Repeating this cycle for each of the different subsets of supports results in randomization in positions following the fixed position in the sequence as a series of library subsets. The resulting subsets are unique only in the fixed position.

3) Once the oligomer synthesis is complete, oligomers are cleaved from the solid support and side chain protecting groups removed by incubation for 1–2 h at room temperature in an appropriate deprotection mixture such as trifluoroacetic acid/trifluoromethanesulfonic acid containing cresol and arylmethyl sulfide as cation scavengers. The supernatant containing the oligomer is then removed from the spent resin. The oligomer is desalted and protecting groups byproducts are removed by HPLC or size exclusion chromatography.

FIG. 8 illustrates a synthetic scheme for the preparation of peptide nucleic acids of predisigned sequence or peptide nucleic acid combinatorial libraries of any desired length utilizing certain sub-monomer building blocks or synthons. One of the synthons is a synthon carrying the individual nucleobases. Another synthon is used for introducing the aminoethyl and still another is used to introduce the acetyl portion. In effecting the synthesis illustrated in FIG. 8, the synthons utilized for this synthesis can be characterized as an acetylnucleobase fragment, e.g. 2-(nucleobase) acetyl chloride; an ethylenediamine fragment, e.g. N-(2-trimethysilylethoxycarbonyl)-1,2-diaminoethane or N-Fmoc-1,2-diaminoethane) hydrochloride; and an haloacetic acid ester or halosulfonic acid ester fragment (where halo is as define previously), e.g. bromoacetic acid ester.

In the synthesis of either known sequence peptide nucleic acids or peptide nucleic acid combinatorial libraries, the assembly of the desired peptide nucleic acid oligomer libraries is carried out, as for instance, by reacting a protected ethylenediamine synthon such as N-(2-trimethylsilylethoxycarbonyl)-1,2-diaminoethane in the presence of an acid scavenger, to an activated solid phase synthesis resin such as methylhydroxycarbonylchloride polystyrene. In one embodiment the resin is activated with a reagent such as phosgene. Next fluoride ion is used to deprotect the terminal amine of the ethylene diamine fragment and the resulting free amine is treated with a haloacetyl synthon such as t-butyl bromoacetate, to couple the two fragments giving a secondary amine and a protected terminal amine thereon. This resulting fragment is next reacted with a 1-haloacetylnucleobase synthon, if a fixed position is desired, and, if a randomized position is desired, in one embodiment of the invention with a mixture of the desired substituted halo acetyl synthons. In a further embodiment of the invention, the resin can be split into portions and each portion reacted with a different 1-haloacetylnucleobase synthon. In one embodiment, each of these, the 1-haloacetylnucleobase or 1-haloacetylnucleobases are added in the presence of an acid scavenger. Particularly suitable as the acid scavenger is a hindered tertiary amine base; however, other acid scavengers can also be used. If the resin is split, it can be recombined. At this point in the synthesis a first peptide nucleic acid unit has been synthesized on the resin. The acetic acid ester portion of the haloacetyl fragment is deprotected to give a carboxyl group which is treated with an another ethylenediamine synthon, in the presence of an appropriate coupling agent, to initiate synthesis of the second peptide nucleic acid unit in the PNA oligomeric structure.

The above iterative process is repeated as many times as is necessary to prepare the desired fully protected, resinattached peptide nucleic acid library with the desired number of fixed and randomized positions. The completed peptide nucleic acid can then be deprotected and cleaved from the resin or cleaved first from the resin and then deprotected. Alternately, for a library of randomly generated peptide nucleic acids, the blocked peptide nucleic acids could remain on the resin and treated with an appropriate biological testing medium to assay for activity.

Variations possible using this method include the use of alternate (substituted) haloacetyl units, such as α-methyl or α-protected hydroxymethyl haloacetyl halide at any position in the oligomer desired. Substitutions or chain length variation in the diaminoethane synthon are also possible and substitution on the acetyl synthon are also considered within the scope of the invention. Variations also include the use of alternate synthons, where any substituent desired to provide binding motifs such as charge, hydrogen bond accepting or donating properties, or hydrophobic and aromatic pi-interactions at any position in the oligomer desired. Substitutions or chain length variation in the synthons are also possible and substitution on the acetyl portion are also with the scope of this method of the invention.

The repeating nature of the synthetic sequence of FIG. 8 can be interrupted at anytime there is a free terminal carboxyl present and an amino acid can be introduced by standard peptide coupling techniques, either as a single fixed amino acid residue or a mixture of amino acids to provide a random position before continuing as described above to the desired length oligomer. This synthetic sequence can also be utilized to extend a normal peptide with peptide nucleic acid units.

In conduction the above processes where the synthons are preformed monomeric peptide nucleic acid units, a preferred group of synthons include N-[2-(thymin-1-yl)acetyl]-N-[2-(t-butyloxycarbonyl)-2-ethylamino]glycine; N-{2-[N$^4$-(benzyloxycarbonyl) cytosin-1-yl]acetyl}-N-[2-(t-butyloxycarbonyl)-2-ethylamino]glycine; N-{2-[N$^4$-(benzyloxycarbonyl)adenin-9-yl]-acetyl}-N-[2-(t-butyloxycarbonyl)-2-ethylamino]glycine; or N-{2-[N$^2$-(benzyloxycarbonyl)guanin-9-yl]acetyl}-N-[2-(t-butyloxycarbonyl)-2-ethylamino]glycine.

EXAMPLE 1

1-(Chlorocarbonylmethyl)thymine oxalyl chloride (6.3 g, 50 mmol) is added dropwise over 5 minutes to a solution of 1-(carboxymethyl)thymine (9.2 g, 50 mmol) dissolved in dichloromethane (200 mL). The reaction is stirred until gas evolution has ceased and then for an additional 2 hours. The reaction mixture is evaporated to an oil.

EXAMPLE 2

1-(Chlorocarbonylmethyl)-N4-(benzyloxycarbonyl) cytosine

Oxalyl chloride (6.3 g, 50 mmol) is added dropwise over 5 minutes to a solution of 1-(carboxymethyl)-N4-(benzyloxycarbonyl)cytosine (15.3 g, 50 mmol) dissolved in dichloromethane (200 mL). The reaction is stirred until gas evolution has ceased and then for an additional 2 hours. The reaction mixture is evaporated to an oil.

EXAMPLE 3

N6-(Benzyloxycarbonyl)-9-(chlorocarbonylmethyl)adenine

Oxalyl chloride (6.3 g, 50 mmol) is added dropwise over 5 minutes to a solution of N6-(benzyloxycarbonyl)-9-(carboxymethyl)adenine (16.6 g, 50 mmol) dissolved in dichloromethane (200 mL). The reaction is stirred until gas evolution has ceased and then for an additional 2 hours. The reaction mixture is evaporated to an oil.

EXAMPLE 4
2-Amino-N2-(benzyloxycarbonyl)-N$^6$-(benzyloxy)-9-(chlorocarbonylmethyl)purine 2-Amino-N2-(benzyloxycarbonyl)-N6-(benzyloxy)-9-(carboxymethyl)purine (21.1 g, 50 mmol) is dissolved in dichloromethane (200 mL) and oxalyl chloride (6.3 g, 50 mmol) is added dropwise over 5 minutes. The reaction is stirred until gas evolution has ceased and then for an additional 2 hours. The reaction mixture is evaporated to an oil.

EXAMPLE 5
N-(Trimethylsilylethoxycarbonyl)-1,2-diaminoethane hydrochloride

N-(t-Butyloxycarbonyl)-1,2-diaminoethane (8.0 g, 50 mmol) is dissolved in THF (200 mL), diisopropylethylamine (6.5 g, 50 mmol) is added and the solution cooled to 0° C. To this cold solution is added dropwise trimethylsilylethoxycarbonylchloride (9.0 g, 50 mmol) over 10 minutes. After stirring an additional 30 minutes the reaction is filtered and the filtrate is evaporated to an oil. This oil is dissolved in 100 mL of diethyl ether and washed with dilute HCl solution (3×25 mL), dried, filtered and evaporated to give an oil. The oil is dissolved in 100 mL of dichloromethane and dry HCl gas is bubbled through the solution for 30 minutes and the reaction stirred for 1 hour. The reaction is diluted with 200 mL of cold diethyl ether and allowed to stand at −5° C. for 12 hours. The colorless solid formed is collected and stored protected from moisture.

EXAMPLE 6
Preparation of Bromoacetoxy Polystyrene Substituted Resin

Hydroxymethyl substituted polystyrene beads (2.0 g, 1.0 mmol/gm loading, 1% crosslinked) is swelled in dichloroethane (150 mL). Triethyl amine (1.0 g, 10 mmol) and bronioacetyl bromide (2.0 g, 10 mmol) are added to the swollen resin. The reaction mixture is stirred for 18 hours then filtered and washed 10 times with 100 mL of dichloromethane, then two times with diethyl ether, and is dried at low vacuum at 40° C. for 18 hours. The free flowing resin powder is used as is—it can be checked for extent conversion by gel phase $^{13}$C-NMR using the procedure of Epton, R., *Polymer*, 1980, 21, 1367–1371.

EXAMPLE 7
Preparation of 2-[(N2-trimethylsilylethoxycarbonyl)-1,2-diaminoethyl]acetoxy Polystyrene Substituted Resin Hydrochloride Salt The resin from Example 6 is swollen in dichloroethane (200 mL) and to this is added N-(trimethylsilylethoxycarbonyl)-1,2-diaminoethane hydrochloride (2.4 g, 10 mmol) and triethyl amine (2.0 g, 20 mmol). The reaction mixture is heated to 40° C. for 18 hours, then cooled and the resin and washed 5 times with dichoromethane (50 mL), then 3 times with diethyl ether (100 mL), and dried at low vacuum at 40° C. for 18 hours. The free flowing resin powder is used as is and can be checked for extent conversion by gel phase $^{13}$C-NMR as per Epton, *Ibid.*

EXAMPLE 8a
Synthesis of Random Secuence-Mixed Monomer Procedure; Addition of Nucleobases The resin from Example 7 is swollen in dichloroethane (200 mL) and to this is added 1-(chlorocarbonylmethyl)thymine, N4-(benzyloxycarbonyl)-1-(chlorocarbonylmethyl)cytosine, N6-(benzyloxycarbonyl)-9-(chlorocarbonylmethyl)adenine, 2-amino-N2-(benzyloxycarbonyl)-N6-(benzyloxy)-9-(chlorocarbonylmethyl)purine (2.5 mmol of each) and triethylamine (2,0 g, 20 mmol). The reaction mixture is heated to 40° C. for 18 hours, then cooled and the resin is washed 5 times with dichoromethane (50 mL), then 3 times with diethyl ether (100 mL), and is dried at low vacuum at 40° C. for 18 hours. The free flowing resin powder is used as is in Example 9.

EXAMPLE 8b
Synthesis of Random Sequence. Split Resin Procedure— Addition of Nucleobases The resin from Example 7 is divided into four equal portions. Each portion is independently swollen in dichloroethane (50 mL). To each portion of the swollen resin is added triethyl amine (0.5 g, 5 mmol) and one of the blocked chloro acetylnucleobases (0.5 mmol), i.e. 1-(chlorocarbonylmethyl)thymine, N4-(benzyloxycarbonyl)-1-(chlorocarbonylmethyl)cytosine, N6-(benzyloxycarbonyl)-9-(chlorocarbonylmethyl)adenine, 2-amino-N2-(benzyloxycarbonyl)-N6-(benzyloxy)-9-(chlorocarbonylmethyl)purine. The reaction mixtures are independently heated to 40° C. for 18 hours, then cooled and the resin is washed 5 times with dichloromethane (50 mL), then 3 times with diethyl ether (100mL), and is dried at low vacuum at 40° C. for 18 hours. The independent portions of the resin are combined together and the free flowing resin powder directly used in Example 9.

EXAMPLE 9
Synthesis of Random Sequence. Mixed Monomer Procedure—Extension of Backbone to 1-[2-(Nucleobase)acetyl]-2-(-1,2-di-aminoethyl)acetoxy on Polystyrene Substituted Resin The resin from Example 8 is swollen in dichloromethane (200 mL) and to this is added tetrabutylammonium fluoride in THF (1.0 M, 1.0 mL) and the suspension stirred for 8 hours. The resin is then washed with dichloromethane containing 0.1% tetrabutyl ammonium chloride (10×25 mL), 5 times with dichloromethane (25 mL), and 3 times with diethyl ether (100 mL), and is dried at low vacuum at 40° C. for 18 hours. The free flowing resin powder is used as is. It is checked for extent conversion by gel phase $^{13}$C-NMR as per Epton, *Ibid.*

EXAMPLE 10
Preraration of 1-[2-(Nucleobase)acetyl]-2-((N2-(2-bromoacetyl)-1,2-diaminoethyl)acetoxy Polystyrene Substituted Resin The resin from Example 9 is swollen in dichloromethane (200 mL) and this is added triethyl amine (1.0 g, 10 mmol) and bromoacetyl bromide (2.0 g, 10 mmol). The reaction mixture is stirred for 18 hours then filtered and washed 10 times with 100 mL of dichloromethane, then two times with diethyl ether, and is dried at low vacuum at 40° C. for 18 hours.

EXAMPLE 11
Preparation of 2'-{[2"-(Trimethylsilylethoxycarbonyl)-1", 2"diaminoethyl]acetyl}-2'-{[1-(nucleobase)acetyl]-1',2'-diaminoethyl}acetoxy Polystyrene Substituted Resin The resin from Example 10 is swollen in dichloromethane (200 mL) and to this is added N-(trimethylsilylethoxycarbonyl)-1,2-diaminoethane hydrochloride (2.4 g, 10 mmol) and triethyl amine (2 g, 20 mmol). The reaction mixture is heated to 40° C. for 18 hours, then cooled and the resin is washed 5 times with dichloromethane, then 3 times with diethyl ether (100 mL), and is dried at low vacuum at 40° C. for 18 hours.

EXAMPLE 12
Addition of Fixed Nucleobase to 2'-{[2-(Trimethylsilylethoxycarbonyl)-1",2"-diaminoethyl]acetyl}-2'-{[1-(nucleobase)-acetyl]-1',2'-diaminoethyl}acetoxy Polystyrene Substituted Resin The resin from Example 11 is swollen in dichloroethane (200 mL) and to this is added 1chlorocarbonylmethyl thymine (2.0 g, 10 mmol) and triethyl amine (2,0 g, 20 mmol). The reaction mixture is heated to 40° C. for 18 hours, then cooled and the resin is washed 5 times with dichoromethane (50 mL), then 3 times with diethyl ether (100 mL), and is dried at low vacuum at 40° C. for 18 hours. The free flowing resin powder is used as is.

EXAMPLE 13
Extension of Backbone and Addition of Further Nucleobases

The resin from Example 12 is deblocked as per the procedure of Example 9. A further known nucleobase is added utilizing the procedures of Examples 10, 11 and 12. A further random nucleobase is added utilizing either the procedure of Example 8a followed by the procedures of Examples 10 and 11 or via the procedure of Example 8b followed by the procedures of Examples 10 and 11. The required number of iterations of the combinations of procedures is effected to complete the oligomer of the desired length.

EXAMPLE 14
Addition of Peptide Nucleic Acid Units to a Peptide

In a variation of the above procedure of Example 13, a peptide is prepared using standard solid phase Merrifield peptide synthesis building the peptide from carboxyl end toward the amine end. The amine terminated peptide is then extended with peptide nucleic acid units utilizing the procedures of Example 13 to either added nucleobases at fixed positions or, using the combinatorial techniques of Example 8a or 8b, to added random nucleobases at any particular position.

EXAMPLE 15
Addition of Amino Acid Units to a Peptide Nucleic Acid Oligomer

In a further variation of the procedure of Example 13, one or more amino acid units is added to the growing peptide nucleic acid oligomer of Example 13. The amine terminated peptide nucleic acid of Example 13 is extended with one or more amino acid units utilizing using an iteration of a standard solid phase Merrifield peptide synthesis condition for each added amino acid. The oligomer can be terminated with the amino acid or a further chain of peptide amino acid units added to the chimeric compound by further iterations of Example 13.

EXAMPLE 16
Deprotection and Isolation of Oligomer

The resin from Example 13, 14 or 15 is swollen in dichloromethane (200 mL) and to this is added tetrabutylammonium fluoride in THF (1.0 M, 1.0 mL) and the suspension stirred for 8 hours. The resin is then washed with dichloromethane containing 0.1% tetrabutyl ammonium chloride (10×25 mL), 5 times with dichloromethane (25 mL). The resin is suspended in dioxane (200 mL) and 1N NaOH (20 mL) is added and the suspension stirred for 12 hours. The resin is washed with 5 times dioxane containing 0.5% 1N HCl . The filtrates are pooled and evaporated to give the oligomeric product. The oligomer product with the side chain protecting groups is further deprotected by treatment with trifluoroacetic acid cresol (7/1 v/v) for 2 hours then diluted with diethyl ether and the precipitate collected to give the crude fully deprotected library.

EXAMPLE 17
1-(Tetramethyl-1,2-disilylethylene)ethylenediamine

In THF (1000 mL) is dissolved ethylene diamine (9 g, 150 mmol) and to this is added 1,2-(dimethylchlorosilyl)ethane (10.5 g, 50 mmol) dropwise over 30 minutes. After stirring for 8 hours, the mixture is diluted with 2L of diethyl ether and the solution is washed with cold saturated sodium bicarbonate solution (5×200 mL), dried, filtered and evaporated giving an oil.

EXAMPLE 18
1-{2-[2-Amino-N2-(Benzyloxycarbonyl)-N6-(benzyloxy)purin-9-yl]-acetyl}-2-(tetramethyl-1,2-disilylethylene)-1,2-ethylenediamine In THF (200 mL) is dissolved 2-amino-N2-(benzyloxycarbonyl)-9-(chlorocarboxymethyl)-N6-(benzyloxy)purine (50 mmol) and triethylamine (50 smmol). To this solution is added dropwise a THF (25 mL) solution of 1-(tetramethyl-1,2-disilylethylene)ethylenediamine (50 mmol) and the resulting solution was stirred for 18 hours. The solution is diluted with 500 mL of diethyl ether and filtered to remove triethylamine hydrochloride, then it is washed with water, followed by saturated sodium bicarbonate solution, dried (MgSO$_4$), filtered, and evaporated to an oil. This oil is purified by crystallization to give a colorless solid.

EXAMPLE 19
1-[2-(Thymin-1-yl)acetyl]-2-(tetramethyl-1,2-disilylethylene)-1,2-ethylenediamine In THF (200 mL) is dissolved 1-(chlorocarbonylmethyl) thymine (50 mmol) and triethylamine (50 mmol). To this solution is added dropwise a THF (25 mL) solution of1-(tetramethyl-1,2-disilylethylene)ethylenediamine (50 mmol) and the resulting solution was stirred for 18 hours. The solution is diluted with 500 mL of diethyl ether and filtered to remove triethylamine hydrochloride, then it is washed with water, followed by saturated sodium bicarbonate solution, dried (MgSO$_4$), filtered, and evaporated to an oil. This oil is purified by crystallization to give a colorless solid.

EXAMPLE 20
1-{2-[N4-(Benzyloxycarbonyl)cytosin-1-yl]acetyl}-2-(tetramethyl-1,2-disilylethylene)-1,2-ethylenediamine In THF (200 mL) is dissolved 1-(chlorocarbonylmethyl)-N4-(benzyloxycarbonyl)cytosine (50 mmol) and triethylamine (50 mmol). To this solution is added dropwise a THF (25 mL) solution of 1-(tetramethyl-1,2-disilylethylene) ethylenediamine (50 mmol) and the resulting solution was stirred for 18 hours. The solution is diluted with 500 mL of diethyl ether and filtered to remove triethylamine hydrochloride, then it is washed with water, followed by saturated sodium bicarbonate solution, dried (MgSO$_4$), filtered, and evaporated to an oil. This oil is purified by crystallization to give a colorless solid.

EXAMPLE 21
1-{2-[N6-(Benzyloxycarbonyl)adenin-9-yl]acetyl}-2-(tetramethyl-1,2-disilylethylene)-1,2-ethylenediamine In THF (200 mL) is dissolved N6-(benzyloxycarbonyl)-9-(chlorocarbonylmethyl) adenine (50 mmol) and triethylamine (50 mmol). To this solution is added dropwise a THF (25mL) solution of 1-(tetramethyl-1,2-disilylethylene) ethylenediamine (50 mmol) and the resulting solution was stirred for 18 hours. The solution is diluted with 500 mL of diethyl ether and filtered to remove triethylamine hydrochloride, then it is washed with water, followed by saturated sodium bicarbonate solution, dried (MgSO$_4$), filtered, and evaporated to an oil. This oil is purified by crystallization to give a colorless solid.

EXAMPLE 22
Preparation of 2-Bromoacetamido MBHA Polystyrene Substituted Resin MBHA polystyrene beads (2.0 g, 1.0 mmol/gm loading, 1% crosslinked) is swelled in dichloroethane (150 mL) and to this is added triethyl amine (1.0 g, 10 mmol) and bromoacetyl bromide (2.0 g, 10 mmol. The reaction mixture is stirred for 18 hours then filtered and washed 10 times with 100 mL of dichloromethane, then two times with diethyl ether, and is dried at low vacuum at 40° C. for 18 hours. The free flowing resin powder is used as is and can be checked for extent conversion by gel phase $^{13}$C-NMR as per Epton, *Ibid.*

EXAMPLE 23
Addition of 1-[2-(Nucleobase) acetyl]-2-(tetramethyl-1,2-disilylethylene)-1,2-ethylenediamine Sub-monomer Unit to Bromoacetamido MBHA Polystyrene Substituted Resin, Fixed Nucleobase Bromoacetamido-MBHA resin (2.0 g, 1.0 mmol/gm loading) is swollen in dioxane (200 mL) and to this is added 1-[2-(thymin-1-yl) acetyl]-2-(tetramethyl-1,2-disilylethylene)-1,2-ethylenediamine (10 mmol), and a 2.0 M THF solution (5 mL) of lithio-tetramethylpiperidine. The suspension is stirred for 8 hours. The resin is then washed with dioxane (10×25 mL), then two-times with diethyl ether, and is dried at low vacuum at 40° C. for 18 hours. The free flowing resin powder is used as is and can be checked for extent conversion by gel phase $^{13}$C-NMR as per Epton, *Ibid.*

EXAMPLE 24
Deblocking of 1-[2-(Nucleobase)acetyl]-2-(tetramethyl-1,2-disilylethylene)-1,2-ethylenediamine Sub-monomer Unit to Bromoacetamido MBHA Polystyrene Substituted Resin The resin from Example 23 is suspended in dichloromethane (100 mL) and 2.0 M tetrabutylammonium fluoride/THF (10 mL) is added and the reaction is stirred for 4 hours. The suspension is stirred for 8 hours. The resin is then washed with dichloromethane (10×25 mL), then two times with diethyl ether, and is dried at low vacuum at 40° C. for 18 hours. The free flowing resin powder is used as is.

EXAMPLE 25
Addition of Further Fixed 1-[2-(Nucleobase)acetyl]-2-(tetramethyl-1,2-disilylethylene)-1,2-ethylenediamine Sub-monomer Unit to PNA Olicomer On Bromoacetamido MBHA Polystyrene Substituted Resin The resin from Example 24 is swollen in dioxane (200 mL) and treated as per Example 22 to added a bromoacetyl moiety to the peptide nucleic acid on the resin. After the addition of the bromoacetamido unit to the first peptide nucleic acid unit, 1-(2-[thyminyl-1-yl]acetyl)-2-(tetramethyl-1,2-disilylethylene)-1,2-ethylenediamine (10 mmol) is added, and a 2.0 M THF solution (10 mL) of lithio-tetramethylpiperidine. The suspension is stirred for 8 hours. The resin is then washed with dioxane (10×25 mL), then two times with diethyl ether, and is dried at low vacuum at 40° C. for 18 hours. The free flowing resin powder is used as is and can be checked for extent conversion by gel phase $^{13}$C-NMR as per Epton, *Ibid.*

EXAMPLE 26
Deblockina of Terminal Peptide Nucleic Acid Unit on MBHA Polystyrene Substituted Resin The resin from Example 25 is suspended in dichloromethane (100 mL) and 2.0 M tetrabutylammonium fluoride/THF (10 mL) is added and the reaction is stirred for 4 hours. The suspension is stirred for 8 hours. The resin is then washed with dichloromethane (10×25 mL), then two times with diethyl ether, and is dried at low vacuum at 40° C. for 18 hours. The free flowing resin powder is used as is.

EXAMPLE 27a
Addition of Random 1-[2-(Nucleobase)acetyl]-2-(tetramethyl-1,2-disilylethylene)-1,2-ethylenediamine Sub-monomer Unit to PNA Olicomer On Bromoacetamido MBHA Polvstyrene Substituted Resin—Mixed Monomer Procedure The resin from Example 24 is swollen in dioxane (200 mL) treated as per example 22 to add a bromoacetyl moiety to the peptide nucleic acid oligomer on the resin and to this is added 1-(2-[thyminyl-1-yl]acetyl)-2-(tetramethyl-1,2-disilylethylene)-1,2-ethylenediamine;1-{2-[2-amino-N2-(benzyloxycarbonyl)-N6-(benzyloxy)purin-9-yl]acetyl}-2-(tetramethyl-1,2-disilylethylene)-1,2-ethylenediamine;1-{2-[N4-(benzyloxycarbonyl)cytosin-1-yl]acetyl}-2-(tetramethyl-1,2-disilylethylene)-1,2-ethylenediamine; and 1-{2-[N6-(benzyloxycarbonyl) adenin-9yl]acetyl}-2-(tetramethyl-1,2-disilylethylene)-1,2-ethylenediamine (2.5 mmol each), and a 2.0 MTHF solution (10 mL) of lithio-tetramethylpiperidine. The suspension is stirred for 8 hours. The resin is then washed with dioxane (10×25 mL), then two times with diethyl ether, and is dried at low vacuum at 40° C. for 18 hours. The free flowing resin powder is used as is and can be checked for extent conversion by gel phase $^{13}$C-NMR as per Epton, *Ibid.*

EXAMPLE 27b
Addition of Random 1-[2-(Nucleobase)acetyl]-2-(tetramethyl-1,2disilylethylene)-1,2-ethylenediamine Sub-monomer Unit to PNA Olipomer On Bromoacetamido MBHA Polystyrene Substituted Resin—Split Resin Procedure The resin from Example 24 is swollen in dioxane (200 mL) treated as per example 22 to add a bromoacetyl moiety to the peptide nucleic acid oligomer on the resin. Then the resin is divided into four equal portions. Each portion is independently swollen in dichloroethane (50 mL). To each portion of the swollen resin is added a 2.0 M THF solution (10 mL) of lithio-tetramethylpiperidine and one of the blocked nucleobase acetyl blocked 1,2-diethylenediamines (0.5 mmol), i.e. 1-(2-[thyminyl-1-yl]acetyl)-2-(tetramethyl-1,2-disilylethylene)-1,2-ethylenediamine;1-{2-[2-amino-N2-(benzyloxycarbonyl)-N6-(benzyloxy)purin-9-yl]acetyl}-2-(tetramethyl-1,2-disilylethylene)-1,2-ethylenediamine;1-{2-[N4-(benzyloxycarbonyl)cytosin-1-yl]acetyl}-2-(tetramethyl-1,2-disilylethylene)-1,2-ethylenediamine; and 1-{2-[N6-(benzyloxycarbonyl) adenin-9-yl]acetyl}-2-(tetramethyl-1,2-disilylethylene)-1,2-ethylenediamine. The suspension is stirred for 8 hours. The resin is then washed with dioxane (10×25 mL), then two times with diethyl ether, and is dried at low vacuum at 40° C. for 18 hours. The individual portions of the resin are recombined together.

EXAMPLE 28
Extension of Backbone and Addition of Further Nucleobases

The resins from Example 27 are deblocked as per the procedure of Example 26. A further known nucleobase is added utilizing the procedures of Example 25 followed by the procedure of Example 26. A further random nucleobase is added utilizing either the procedure of Example 27a followed by the procedure of Examples 26 or via the procedure of Example 27b followed by the procedure of Example 26. The required number of iterations of the combinations of procedures is effected to complete the oligomer of the desired length.

EXAMPLE 29
Addition of Peptide Nucleic Acid Units to a Peptide

In a variation of the above procedure of Example 28, a peptide is prepared using standard solid phase Merrifield peptide synthesis building the peptide from carboxyl end toward the amine end. The amine terminated peptide is then extended with peptide nucleic acid units utilizing the procedures of Example 22 coupled with Examples 23 or 25 to either added nucleobases at fixed positions or, using Example 22 coupled with the combinatorial techniques of Example 27a or 27b, to added random nucleobases at any particular position. After addition of the peptide nucleic acid unit, its terminal amine is deprotected via the procedure of Example 26.

EXAMPLE 30
Addition of Amino Acid Units to a Peptide Nucleic Acid Oligomer

In a further variation of the procedures of Example 28 and 29, one or more amino acid units is added to the growing peptide nucleic acid oligomer. The amine terminated peptide nucleic acid of Example 26 is extended with one or more amino acid units utilizing using an iteration of a standard solid phase Merrifield peptide synthesis condition for each added amino acid. The oligomer can be terminated with the amino acid or a further chain of peptide amino acid units added to the chimeric compound by further iterations of Example 28.

EXAMPLE 31
Removal From Resin and Deblocking

The resin from Examples 28, 29 or 30 is cleaved by the procedure described in Stewart and Young, Solid Phase Peptide Synthesis (1984), page 88. After evaporating the HF the residue is worked up in the standard fashion, dissolved in methanol (20 mL) with 10% acetic acid in a hydrogenation bottle to which is added 0.1 g of 10% Pd on barium sulfate. The bottle is pressurized with hydrogen and shaken for 18 hours and vented, filtered through celite and evaporated to a solid.

EXAMPLE 32
1-{2-[N$^2$-(Benzyloxycarbonyl)-N$^6$-benzyloxy)-2-aminopurin-9-yl]carbonylmethyl}-3-oxo-morpholine In THF (200 mL) is dissolved 2-amino-N$^2$(benzyloxycarbonyl)-N6-(benzyloxy)-9-(chlorocarboxymethyl)purine (50 mmol) and triethylamine (50 mmol). To this solution is added dropwise a THF (25 mL) solution of 3-oxo-morpholine (50 mmol) and the resulting solution was stirred for 18 hours. The solution is diluted with 500 mL of diethyl ether and filtered to remove triethylamine hydrochloride, then it is washed with water, followed by saturated sodium bicarbonate solution, dried (MgSO$_4$), filtered, and evaporated to an oil. This oil is purified by crystallization to give a colorless solid.

EXAMPLE 33
1-{2-[N6-(benzyloxycarbonyl)adenin-9-yl]carbonylmethyl}-3-oxo-morpholine In THF (200 mL) is dissolved N6-(benzyloxycarbonyl)-9-(chlorocarbonylmethyl) adenine (50 mmol) and triethylamine (50 mmol). To this solution is added dropwise a THF (25 mL) solution of 3-oxo-morpholine (50 mmol) and the resulting solution was stirred for 18 hours. The solution is diluted with 500 mL of diethyl ether and filtered to remove triethylamine hydrochloride, then it is washed with water, followed by saturated sodium bicarbonate solution, dried (MgSO$_4$), filtered, and evaporated to an oil. This oil is purified by crystallization to give a colorless solid.

EXAMPLE 34
1-{2-[N4-(Benzyloxycarbonyl)cytosin-1-yl]carbonylmethyl}-3-oxo-morpholine In THF (200 mL) is dissolved N4-(benzyloxycarbonyl)-1-(chlorocarbonylmethyl)cytosine (50 mmol) and triethylamine (50 mmol). To this solution is added dropwise a THF (25 mL) solution of 3-oxo-morpholine (50 mmol) and the resulting solution was stirred for 18 hours. The solution is diluted with 500 mL of diethyl ether and filtered to remove triethylamine hydrochloride, then it is washed with water, followed by saturated sodium bicarbonate solution, dried (MgSO$_4$), filtered, and evaporated to an oil. This oil is purified by crystallization to give a colorless solid.

EXAMPLE 35
1-[2-(Thymin-1-yl)lcarbonylmethyll-3-oxo-morpholine

In THF (200 mL) is dissolved 1-(chlorocarbonylmethyl)thymine (50 mmol) and triethylamine (50 mmol). To this solution is added dropwise a THF (25 mL) solution of 3-oxo-morpholine (50 mmol) and the resulting solution was stirred for 18 hours. The solution is diluted with 500 mL of diethyl ether and filtered to remove triethylamine hydrochloride, then it is washed with water, followed by saturated sodium bicarbonate solution, dried (MgSO$_4$), filtered, and evaporated to an oil. This oil is purified by crystallization to give a colorless solid.

EXAMPLE 36
Addition of N-[2-(Thymin-1-yl)acetyl]-N-(hydroxyethyl)glycyl Unit to Resin MBHA resin (2.0 g, 1.0 mmol/gm loading) is swollen in dichloromethane (200 mL) and to this is added 1-[2-(thymin-1-yl) carbonylmethyl]-3-oxo-morpholine and the suspension stirred for 8 hours. The resin is then washed with dichloromethane (10×25 mL), then two times with diethyl ether, and is dried at low vacuum at 40° C. for 18 hours. The free flowing resin powder is used as is and can be checked for extent conversion by gel phase $^{13}$C-NMR as per Epton, *Ibid.*

EXAMPLE 37
Mitsunobu Conversion of Terminal Resin Bound Structure to N-[2-(Thymin-1-yl)acetyl]-N-(aminoethyl)glycyl unit The resin from Example 36 is swollen in dioxane (200 mL) and to this is added triphenylphosphine (10 mmol), diethylazodicarboxylate (10 mmol), and bis(t-butoxycarbonyl)imide (10 mmol). The suspension is heated to 60° C. and stirred for 12 hours. This suspension is filtered, washed with dioxane (5×100 mL), and resuspended in dichloromethane (200 mL). To this is added trifluoroacetic acid (30 mmol) and the suspension is stirred for 6 hours, then filtered and the resin is washed 10 times with dichloromethane (100 mL) then two times with diethyl ether, and is dried at low vacuum at 40° C. for 18 hours. The free flowing resin powder is used as is.

EXAMPLE 38
Addition of Additional Fixed Peptide Nucleic Acid Unit to Growing Olipomer On Resin The resin from Example 37 is swollen in dichloromethane (200 mL) and to this is added a 1-[2-(nucleobase)-carbonylmethyl]-3-oxo-morpholine synthon (either 1-[2-(thymin-1-yl)carbonylmethyl]-3-oxo-morpholine, 1-{2-[N4-(benzyloxycarbonyl)cytosin-1-yl)carbonylmethyl}-3-oxo-morpholine, 1-{2-[2-amino-N2-(benzyloxycarbonyl)-N6-(benzyloxy)purin-9-yl]carbonylmethyl}-3-oxo-morpholine or 1-{2-[N6-(benzyloxycarbonyl)adenin-9-yl]carbonylmethyl}-3-oxo-morpholine) and the suspension is stirred for 8 hours. The resin is then washed with dichloromethane (10×25 mL), then two times with diethyl ether. The resin is re-swollen in dioxane (200 mL) and to this is added triphenylphosphine (10 mmol), diethylazodicarboxylate (10 mmol), and bis (t-butoxycarbonyl) imide (10 mmol). The suspension is heated to 60° C. and stirred for 12 hours. This suspension is filtered, washed with dioxane (5×100 mL), and resuspended in dichloromethane (200 mL). To this is added trifluoroacetic acid (30 mmol) and the suspension is stirred for 6 hours, then filtered and the resin is washed 10 times with dichloromethane (100 mL) then two times with diethyl ether.

EXAMPLE 39a
Addition of Random 1-[2-(Nucleobase)carbonylmethyl]-3-oxo-morpholine Synthon Unit to PNA Oligomer On MBHA Polystyrene Substituted Resin—Mixed Monomer Procedure The resin from Example 37 is swollen in dichloromethane (200 mL) and to this is added a mixture of 1-(2-(thymin-1-yl)carbonylmethyl]-3-oxo-morpholine, 1-{2-[N4-(benzyloxycarbonyl)cytosin-1-yl]carbonylmethyl}-3-oxo-morpholine, 1-{2-[2-amino-N2-(benzyloxycarbonyl)-N6-(benzyloxy)purin-9-yl]carbonylmethyl}-3-oxo-morpholine or 1-{2-[N6-(benzyloxy-carbonyl)adenin-9-yl]carbonylmethyl}-3-oxo-morpholine (equal molar amounts) and the suspension is stirred for 8 hours. This suspension is filtered, washed with dioxane (5×100 mL), and resuspended in dichloromethane (200 mL). To this is added trifluoroacetic acid, (30 mmol) and the suspension is stirred for 6 hours then filtered and the resin is washed 10 times with dichloromethane (100 mL) then two times with diethyl ether.

EXAMPLE 39b
Addition of Random 1-[2-(Nucleobase)carbonylmethyl]-3-oxo-morpholine Synthon Unit to PNA Oligomer On MBHA Polystyrene Substituted Resin—Split Resin Procedure The resin from Example 37 is divided into four equal portions. Each portion is independently swollen in dichloroethane (50 mL). To each portion of the swollen resin is added one of the blocked nucleobases synthons 1-(2-(thymin-1-yl)carbonylmethyl]-3-oxo-morpholine, 1-{2-[N4-(benzyloxycarbonyl)-cytosin-1-yl]carbonylmethyl}-3-oxo-morpholine, 1-{2-[2-amino-N 2-(benzyloxycarbonyl)-N6-(benzyloxy)purin-9-yl]carbonylmethyl}-3-oxo-morpholine or 1-{2-[N6-(benzyloxycarbonyl)adenin-9-yl]carbonylmethyl}-3-oxo-morpholine and the suspension is stirred for 8 hours. The suspensions are filtered, washed with dioxane (5×10 mL), resuspended in dichloromethane (200 mL) and combined. To this is added trifluoroacetic acid (30 mmol) and the suspension is stirred for 6 hours then filtered and the resin is washed 10 times with dichloromethane (100 mL) then two times with diethyl ether.

EXAMPLE 40
Extension of Backbone and Addition of Further Nucleobases

The resins from Examples 38 or 39 are treated as per the procedure of Example 37 to convert the terminal hydroxyl moieties to terminal amine moieties. A further known nucleobase is added utilizing the procedures of Example 36 followed by the procedure of Example 37. A further random nucleobase is added utilizing either the procedure of Example 39a followed by the procedure of Example 36 or via the procedure of Example 39b followed by the procedure of Example 36. The required number of iterations of the combinations of procedures is effected to complete the oligomer of the desired length.

EXAMPLE 41
Addition of Peptide Nucleic Acid Units to a Peptide

In a variation of the above procedure of Example 40, a peptide is prepared using standard solid phase Merrifield peptide synthesis building the peptide from carboxyl end toward the amine end. The amine terminated peptide is then extended with peptide nucleic acid units utilizing the procedures of Example 37 coupled with Example 38 to added nucleobases at fixed positions or, using the combinatorial techniques of Example 39a or 39b coupled with the procedure of Example 36, to added random nucleobases at any particular position.

EXAMPLE 42
Addition of Amino Acid Units to a Peptide Nucleic Acid Oligomer

In a further variation of the procedures of Example 40 and 41, one or more amino acid units is added to the growing peptide nucleic acid oligomer. The amine terminated peptide nucleic acid is extended with one or more amino acid units utilizing an iteration of a standard solid phase Merrifield peptide synthesis conditions for each amino acid added. The oligomer can be terminated with the amino acid or a further chain of peptide amino acid units added to the chimeric compound by further iterations of Example 40.

EXAMPLE 43
Cleavage of Peptide Nucleic Acid Oligomer From Resin

Upon completion of the complete synthesis of the desired length PNA oligomer, the resin from Example 40 is dried by blowing argon across it for 15 minutes. It is washed twice with 3 ml portions of TFA for 2 minutes. The following reagents are added in order: 0.333 ml of m-cresol, 1.0 ml of dimethyl sulfide, and 1.83 ml of TFA. While the flask is shaking 0.167 ml of trifluoromethane sulfonic acid (TFMSA) is added dropwise. This mixture is shaken for 1 hour. At the end of that time the resin is drained and washed twice with 3 ml portions of TFA and four 3 ml portions of ethyl ether. The deprotected PNA attached to the resin is dried with flowing argon. To cleave the PNA off the resin the following reagents are added in order: m-cresol 0.417 ml, TFA 3.33 ml and TFMSA 0.417 ml added dropwise with shaking. After 1 hour, the solution is drained into 25 ml of ether, and the resin washed with a single 3 ml portion of TFA. The acidic ether solution is concentrated to an oil, then diluted with 5 ml of water and extracted with 10 ml of ether until clear. HPLC analysis of the product is examined by HPLC using an Alltech MMRP C18/cation exchange column 250 mm ×4.6 mm eluting with pH 5 Citrate buffer and a gradient going from 0–20% acetonitrile over 20 minutes with a flow rate of 1.5 ml/minute.

EXAMPLE 44
Random Peptide Nucleic Acid; Pre-formed Monomer Synthons—Split Resin Method PNA backbone oligomers are synthesized using the standard peptide nucleic acid chemistry. Each PNA residue (2 mmol each), N-[2-(thymin-1-yl)acetyl]-N-[2-(t- butyloxycarbonyl)-2-ethylamino]glycine; N-{2-[N4-(benzyloxycarbonyl)cytosin-1-yl]acetyl}-N-[2-(t-butyloxycarbonyl)-2-ethylamino-[glycine; N-{2-[N4-(benzyloxycarbonyl)adenin-9-yl]acetyl}-N-[2-(t-butyloxycarbonyl)-2-ethylamino]glycine; and N-{2-[N2-(benzyloxycarbonyl)guanin-9-yl]acetyl}-N-[2-(t-butyloxycarbonyl)-2-ethylamino]glycine, was individually reacted to completion with an aliquot of a solid support (50 $\mu$mol), carrying a lysine, available commercially, where the terminal Boc protecting group has been removed by treating the resin twice with neat trifluoroacetic acid (2×1 mL for 5 min), followed by washing the resin with DMF/pyridine, followed by DMF, then dichloromethane (each wash is 2×10 mL). The coupling is done in DMF/pyridine (2 mL) using TBTU (500 mol %), diisopropylethylamine (1000 mol %) and the incoming PNA monomer (400 mol %). Then, the aliquots of the residue-solid support are separately washed with DMF, followed by dichloromethane (each wash is 2×10 mL). The separate aliquots are combined and thoroughly mixed by suspension and agitation in dichloromethane, then filtered, dried under vacuo and realiquoted into 4 subfractions. For the next position, each residue pool or aliquot is deprotected with TFA (2×2 mL for 5 min), then it is coupled again, mixed and realiquoted as described above. This is continued until the amino-terminal fixed position designated X is coupled, X-N-N-N-S, after which the pools are kept separate. The resin is cleaved by the procedure described in Stewart and Young, Solid Phase Peptide Synthesis (1984). After removing the TFA/TFMSA mixture from the beads and precipitating the library from diethyl ether, the solid residue is worked up in the standard fashion to give separately the library pools with one fixed position each.

These pools, one for every type of X residue, are assayed for activity. The most active residue is kept fixed (for example A) and another round of synthesis is done, this time A-X-N-N-S. The synthesis procedure is the same as the first round. Coupling, mixing and realiquoting is continued until after the fixed position designated X is coupled. At this point aliquots are kept separate. The final residue, A, is coupled to each portion. By keeping the pools separate, one obtains pools which are unique at one fixed position. This synthesis technique is continued until the entire sequence is determined.

EXAMPLE 45
Random Pertide Nucleic Acid; Pre-formed Monomer Synthons—Mixed Monomers Method PNA backbone oligomers are be synthesized using the standard peptide chemistry. Each PNA residue, (2 mmol each), N-[2-(thymin-1-yl) acetyl]-N-(2-(t-butyloxycarbonyl)-2-ethylamino]glycine; N-{2-[N4-(benzyloxycarbonyl)cytosin-1-yl]acetyl}-N-[2-(t-butyloxycarbonyl)-2-ethylamino]glycine; N-{2-[N$^4$-(benzyloxycarbonyl)adenin-9-yl]acetyl}-N-[2-(t-butyloxycarbonyl)-2-ethylamino]glycine; N-{2-[N2-(benzyloxycarbonyl)guanin-9-yl]acetyl}-N-[2-(t-butyloxycarbonyl)-2-ethylamino]glycine,was combined by dissolving together in DMF (3 mL) reacted to completion with an aliquot of a solid support (50 $\mu$mol), carrying a lysine, available commercially, where the terminal Boc protecting group has been removed by treating the resin twice with neat trifluoroacetic acid (2×1 mL for 5 min), followed by washing the resin with DMF/pyridine, followed by DMF, then dichloromethane (each wash is 2×10 mL). The coupling is done in DMF/pyridine(2 mL) using TBTU (500 mol % calculated for total carboxylic acid content), diisopropylethylamine (1000 mol %) and the incoming PNA monomer (400 mol % of each monomer). Then, the residue-solid support are washed with DMF, followed by dichloromethane (each wash is 2×10 mL). For the next position, the pool was deprotected with TFA (2×2 mL for 5 min), then it is coupled again as described above. This is continued until the amino-terminal fixed position designated X is coupled. At this point the resin is divided into four pools and each is coupled with a single peptide nucleic acid monomer, X-N-N-N-S, after which the pools are kept separate. The resin pools are cleaved by the procedure described in Stewart and Young, Solid Phase Peptide Synthesis (1984). After removing the TFA/TFMSA mixture from the beads and precipitating the library from diethyl ether, the solid residue is worked up in the standard fashion to give separately the library pools with one fixed position each.

These pools, one for every type of X residue, are assayed for activity. The most active residue is kept fixed (for example A) and another round of synthesis is done, this time A-X-N-N-S. The synthesis procedure is the same as the first round. Coupling, mixing and realiquoting is continued until after the fixed position designated X is coupled. At this point aliquots are kept separate. The final residue, A, is coupled to each portion. By keeping the pools separate, one obtains pools which are unique at one fixed position. This synthesis technique is continued until the entire sequence is determined.

EXAMPLE 46
Random Peptide Nucleic Acid Containing Internal Amino Acid Unit: Pre-formed Monomer Synthons—Split Resin Method PNA backbone oligomers are be synthesized using the standard peptide chemistry. Each PNA residue, (2 mmol each), N-[2-(thymin-1-yl)acetyl]-N-[2-(t-butyloxycarbonyl)-2-ethylamino]glycine; N-{2-[N4-(benzyloxycarbonyl)cytosin-1-yl]acetyl}-N-[2-(t-butyloxycarbonyl)-2-ethylamino]glycine; N-{2-[N$^4$-(benzyloxycarbonyl)adenin-9-yl]acetyl}-N-[2-(t-butyloxycarbonyl)-2-ethylamino]glycine; N-{2-[N2-(benzyloxycarbonyl)guanin-9-yl]acetyl}-N-[2-(t-butyloxycarbonyl)-2-ethylamino]glycine,was combined by dissolving together in DMF (3 mL) reacted to completion with an aliquot of a solid support (50 $\mu$mol), carrying a lysine, available commercially, where the terminal Boc protecting group has been removed by treating the resin twice with neat trifluoroacetic acid (2×1 mL for 5 min), followed by washing the resin with DMF/pyridine, followed by DMF, then dichloromethane (each wash is 2×10 mL). The coupling is done in DMF/pyridine (2 mL) using TBTU (500 mol % calculated for total carboxylic acid content), diisopropylethylamine (1000 mol %) and the incoming PNA monomer (400 mol % of each monomer). Then, the residue-solid support are washed with DMF, followed by dichloromethane (each wash is 2×10 mL). For the next position, the pool was deprotected with TFA (2×2 mL for 5 min), then it is coupled again as described above. The resin is separated into 4 separate but equal aliquots, the deprotected with TFA (2×2 mL for 5 min.), washed as above and reacted separately with solutions of N-(t-butyloxycarbonyl) amino acid, i.e. glycine, phenylalanine, O-benzylaspartic acid, and N-benzyloxycarbonyl lysine, each activated by dissolving 2 mmol of amino acid in DMF/pyridine (1 mL) containing 3 mmol TBTU and 500 mmol DIPEA. After allowing the reactions to proceed for 15 minutes the resin is washed thoroughly as described above. The aliquots are kept separate. Each is individual subjected to the mixed monomers method to complete the synthesis. The resin pools are cleaved by the procedure described in Stewart and Young, Solid Phase Peptide Synthesis (1984). After removing the

EXAMPLE 47
(N1-Thymine)-2-Acetic Acid

Methyl bromoacetate (25.5 g, 15.2 ml, 160 mmol) was added to a suspension of $K_2CO_3$ (44.2 g, 320 mmol) and thymine (20.2 g, 160 mmol) in 500 ml dry DMF with stirring overnight. The suspension was filtered and the solvent removed under reduced pressure. The residue was suspended in 120 ml $H_2O$ and 30 ml 4 N HCl, stirred for 30 minutes and filtered again. The solid was suspended in 250 ml $H_2O$, to which was added 100 ml 2.5 M NaOH. The solution was heated to boiling, cooled and acidified to pH 1 with concentrated HCl. The precipitate was dried in vacuo to give 13.6 g (73.6 mmol, 46%) pure product. $^1$H NMR: (DMSO-$d_6$, 200 MHz) δ 7.48 (s, 1H, H6), 4.37 (s, 2H, $CH_2$), 1.76 (s, 3H, $CH_3$).

EXAMPLE 48
N-4-Benzoyl-1-cytosine-2-acetic acid

Cytosine hemihydrate (12.0 g, 100 mmol) was coevaporated with pyridine and resuspended in 250 ml dry pyridine. Benzoyl chloride (58 ml, 70.3 g, 500 mmol) was added dropwise (exothermic). The solution was stirred at RT overnight, and water (50 ml) carefully added. The solvent was evaporated, and the residue dissolved in 700 ml $H_2O$ containing 55 g NaOH. The solution was stirred for 1 h after complete dissolution of the material. Concentrated HCl was then added to pH 4.0, the white precipitate was collected and boiled in 1 liter EtOH, cooled to RT and filtered to give 16.1 g product (75%).

To a suspension of N-4-Benzoylcytosine (15.0 g, 69.7 mmol) and $K_2CO_3$ (9.7 g, 70 mmol) in 500 ml DMF was added methyl bromoacetate (6.6 ml, 10.7 g, 70 mmol). The suspension was stirred vigorously for 3 days, filtered and evaporated. The residue was treated with water (120 ml), and 10 ml 4N HCl for 15 min, and the solid collected by filtration. The residue was resuspended in 120 ml water, and 60 ml 2N NaOH added. The suspension was stirred at RT for 45 min, until all the solids had dissolved. The solution was acidified to pH 2 with conc HCl, filtered, and the solid dried in vacua at 60° C. to give 11.6 g product (61%).

EXAMPLE 49
(9-Adenine)-2-Acetic Acid Ethyl Ester

Sodium hydride (8.20 g 60% in oil, 205 mmol) was added to a suspension of adenine (25.0 g, 185 mmol) in 500 ml DMF. After vigorous stirring for 2 hours using a mechanical stirrer, $H_2$ evolution stopped and a thick slurry was obtained. Ethyl bromoacetate (55.6 g, 36.9 ml, 333 mmol) was added dropwise over 3 hours, and stirring continued for a further 1 hour. Water (10 ml) and $H_2SO_4$ were added to pH 4. The solvent was evaporated and the residue suspended in 500 ml $H_2O$, filtered and washed with water. The residue was recrystallized from 400 ml ethanol to give 23.8 g (108 mmol, 58%) pure product.

EXAMPLE 50
(N6-Benzoyl-9-Adenine)-2-Acetic Acid

To a suspension of (9-adenylyl)-2-acetic acid ethyl ester (6.06 g, 27.4 mmol) in 250 ml dry pyridine was added benzoyl chloride (9.60 ml, 11.6 g, 82 mmol), and the solution stirred for 4 hours at room temperature. Methanol (25 ml) was added and the solvents evaporated. The residue was dissolved in ethyl acetate (2×250 ml), washed with 0.1 N HCl, $H_2O$, saturated $NaHCO_3$, brine, and dried with $Na_2SO_4$. The organic extracts were evaporated and the solid residue was redissolved in 250 ml THF at 0° C., to which was added 100 ml 1M NaOH. The solution was stirred at 0° C. for 1 hour and acidified to pH 1 with concentrated HCl, and the aqueous portion extracted once with ether. The product, which began to crystallize almost immediately, was collected by filtration to yield 4.96 g (61%). $^1$H NMR: (DMSO-$d_6$, 200 MHz) δ 8.86, 8.84 (d, H2, H8), 8.1 (d, 2H, J=7.0 Hz, ArH), 7.69–7.58 (m, 3H, Ar-H), 5.22 (s, 2H, $CH_2$).

EXAMPLE 51
N-Trimethylsilylethoxycarbonyl-1,2-DiaminoethaneHydrochloride

N-t-Butyloxycarbonyl-1,2-diaminoethane (8.0 g, 50 mmol) is dissolved in THF (200 mL) and diisopropylethylamine (6.5 g, 50 mmol) is added and the solution cooled to 0° C. To this cold solution is added dropwise trimethylsilylethoxycarbonylchloride (9.0 g, 50 mmol) over –0 minutes. After stirring an additional 30 minutes the reaction is filtered and the filtrate is evaporated to an oil. This oil is dissolved in 100 mL of diethyl ether and washed with dilute HCl solution (3×25 mL), dried, filtered and evaporated to give an oil. The oil is dissloved in 100 mL of dichloromethane and dry HCl gas is bubbled through the solution for 30 minutes and the reaction stirred for 1 hour. The reaction is diluted with 200 mL of cold diethyl ether and allowed to stand at –5° C. for 12 hours. The colorless solid formed is collected and stored protected from moisture.

EXAMPLE 52
Synthesis of Chlorocarboxymethyl Polystyrene Substituted Resin

Hydroxymethyl substituted polystyrene beads (2.0 g, 1.0 mmol/g loading 1% crosslinked) is swelled in dichloroethane (150 mL) and to this is added phosgene (1.0 g, 10 mmol). The reaction was stirred for 20 hours while periodocally bubbling nitrogen through the suspension to sweep of HCl and drive the reaction to completion. The reaction mixture is then filtered and washed 3 times with 100 mL of dichloromethane, then two times with diethyl ether, and is dried at low vacuum at 40° C. for 18 hours. The free flowing resin powder is used.

EXAMPLE 53
Synthesis of N2-((N1-Trimethylsilylethoxycarbonyl)-1,2-diaminoethane)methylcarboxy Polystyrene Substituted Resin The resin from Example 52 is swollen in dichloroethane (200 mL) and to this is added N-trimethylsilylethoxycarbonyl-1,2-diaminoethane hydrochloride (2.4 g, 10 mmol), [O-(7-azabenzotriazol-1-yl)-1,1,3,3-tetramethyluronium hexafluorophosphate (3.8 g, 10 mmol), and triethylamine (2.0 g, 20 mmol). The reaction mixture is heated to 35° C. for 18 hours, then cooled and the resin is washed 5 times with dichoromethane (50 mL), then 3 times with diethyl ether (100 mL), and is dried at low vacuum at 40° C. for 18 hours.

EXAMPLE 54

N2-(1,2-diaminoethane)carboxymethyl Polystyrene Substituted Resin

The resin from Example 53 is swollen in dichloromethane (200 mL) and to this is added tetrabutylammonium fluoride in THF (1.0 M, 1.0 mL) and the suspension stirred for 8 hours. The resin is then washed with dichloromethane containing 0.1% tetrabutyl ammonium chloride (10×25 mL), 5 times with dichloromethane (25mL), and 3 times with diethyl ether (100 mL), and is dried at low vacuum at 40° C. for 18 hours. The free flowing resin powder is used as is and can be checked for extent conversion by gel phase $^{13}$C-NMR according to E. Girard.

EXAMPLE 55

Synthesis of N2-((N1-t-butyl acetic acid ester)-1,2-diaminoethane)carboxymethyl Polystyrene Substituted Resin The resin from Example 54 is swollen in dichloroethane (20 OmL) and to this is added t-butyl bromoacetate (10 mmol) and triethylamine (2.0 g, 20 mmol). The reaction mixture is heated to 30° C. for 18 hours, then cooled and the resin is washed 5 times with dichoromethane (50 mL), then 3 times with diethyl ether (100 mL), and is dried at low vacuum at 40° C. for 18 hours. The free flowing resin powder is used as is.

EXAMPLE 56

Synthesis of N2-[((N1-(N1-acetyl thymine))-N1-t-butyl acetic acid ester)-1,2-diaminoethane]carboxymethyl Polystyrene Substituted Resin The resin from Example 55 is swollen in dichloroethane (200 mL) and to this is added 1-carboxymethyl thymine (2.0 g, 10 mmol) and triethylamine (2,0 g, 20 mmol). The reaction mixture is heated to 40° C. for 18 hours, then cooled and the resin is washed 5 times with dichoromethane (50 mL), then 3 times with diethyl ether (100 mL), and is dried at low vacuum at 40° C. for 18 hours. The free flowing resin powder is used as is.

EXAMPLE 57

Synthesis of N2-[((N1-(N1-acetyl thymine))-N1-acetic acid)-1,2-diaminoethane]carboxymethyl Polystyrene Substituted Resin The resin from Example 56 is swollen in dichloromethane (200 mL) and to this is added trifluoroacetic acid (20 mL). The reaction is stirred at room temperature for 4 hours then filtered and washed 5 times with dichloromethane (50 mL), then 3 times with diethyl ether (100 mL) and is dried at low vacuum at 40° C. for 18 hours. The free flowing powder is used as is.

EXAMPLE 58

Synthesis of N2-[((N1-(N1-acetyl thymine))-N1-(acetyl-N1-1,2-diaminoethane-N2-trimethylsilylethoxycarbonyl)-1,2-diaminoethane]carboxymethyl Polystyrene Substituted Resin The resin from Example 57 is swollen in dichloromethane (200 mL) and to this is added a uronium salt (10 mmol), diisopropylethyl amine (25 mmol), and N-trimethylsilylethoxycarbonyl-1,2-diaminoethane hydrochloride (2.4 g, 10 mmol). The reaction is stirred at room temperature for 4 hours then filtered and washed 5 times with dichloromethane (50 mL), then 3 times with diethyl ether (100 mL) and is dried at low vacuum at 40° C. for 18 hours. The free flowing powder is used as is.

EXAMPLE 59

PNA Synthesis Termination Step

PNA monomers are added via the sub-monomer approach to a growing PNA oligomer by repeating Examples 54 through 58. When the desired length is reached the resin is suspended in trifluoromethanesulfonic/trifluoroacetic acid m-cresol (1/8/1, 30 mL) and allowed to stand for 3 hours. The solution is separated from the spent resin by filtration. The acids are diluted with diethyl ether (200 mL) and the precipit ated solid collected, washed with ether and dried to give the crude PNA product. This crude PNA product is purified using standard techniques to obtain the pure PNA oligomer.

EXAMPLE 60

Synthesis of $H_2N$-Gly-AT-Lys-$NH_2$

In a shaker flask, 75 mg, 50 μmoles, of MBHA α-Boc-ε-(2-chlorobenzyloxycarbonyl)-lysine resin was washed with 5 ml of dichloromethane (DCM), for 15 minutes. The DCM was drained and 5 ml of dimethyl formamide (DMF) was added and the flask shaken for another 15 minutes. Again the DMF was drained and the resin then washed with 3 ml of a 1:1 solution of DCM:DMF for 1 minute. This was repeated an additional 2 times. The t-butoxy carbonyl group (Boc) was removed from the a amine of the lysine in the following fashion. The resin was treated with 1 ml of DCM and 3 ml of a 5% m-cresol in trifluoroacetic acid, (TFA), for 2 minutes; this is repeated three times, draining the solution after each cleavage. The resin is then washed with 3 ml of 1:1 DCM:DMF for 1 minute repeated 3 times, and 3 ml of pyridine (pyr), for 1 minute repeated 4 times. In a small vial 77 mg, 200 μmoles, of thymine PNA monomer and 58 mg, 180 μmoles of 2-(1H-benzotriazole-1-yl)-1,1,3,3-tetramethyluronium tetraf luoroborate, (TBTU) were dissolved in 1 ml of a 1:1 solution of DMF/pyr. To this solution 80 μL, 834 μmoles, of dutsopropyl ethyl amine (DIEA), was added and the solution stirred for 1 minute before adding to the resin. The mixture was shaken for 20 minutes. At the end of the time the solution was drained and the resin was wash ed with 3 mL of pyr for 1 minute repeated 3 times. A Kaiser test was performed on a few of the beads by adding 2 drops each of the following solutions: 1) 0.5 g of ninhydrin in 10 ml of n-butanol; 2) 2 tnL of a 0.01 N KCN in 98 mL of pyr; and 3) 8 g phenol dissolved in 2 mL of n-butanol. The solution was heated at 95° C. for 5 minutes. If the beads had any blue color, a positive Kaiser, the resin was recoupled using the same method as above, without the TFA treatment. Generally the beads are clear and colorless, with the solution taking on a light orange color for a negative test. Any free amines were then capped using 1-(benzyloxycarbonyl)-3-methylimidazolium trifluoromethane sulfonate (Rapoport's Reagent). In a small vial 150 mg, 411 μmoles, of Rapoport's reagent was dissolved in 1 mL of DMF and added to the resin, and shaken for 5 minutes. The resin was then drained and washed with 3 mL of pyr three times for 1 minute and 3 mL of the DCM/DMF solution.

The t-butoxy carbonyl was removed as above with TFA, and the second monomer, adenine PNA monomer, was coupled using 106 mg, 200 μmoles of PNA adenine monomer. Capping and washing procedures are as stated in the above paragraph. The final residue, glycine was coupled using the following amounts. In a vial 88 mg, 500 μmoles of t-Boc-Glycine and 153 mg, 477 μmoles of TBTU and 160 mL of DIEA were activated and added to the resin. After coupling for 20 minutes the resin was drained and washed and capped as above.

EXAMPLE 61

$H_2N$-Gly-CT-Lys-$NH_2$

The procedure of Example 60 was repeated coupling first the thymine PNA monomer exactly described in Example 60. The second coupling was performed as above, substituting of cytosine PNA monomer (101 mg, 200 μmoles). The coupling with glycine, cleavage, and analysis were repeated exactly as found in Example 60.

EXAMPLE 62

H$_2$N-Gly-CT-Lys-NH$_2$

The procedure of Example 60 was followed except that guanine PNA monomer (109 mg, 200 μmoles) was substituted for the adenine PNA monomer.

EXAMPLE 63

H$_2$N-Gly-TT-Lys -NH$_2$

The procedure of Example 60 was followed except that thymine PNA monomer (109 mg, 200 μmoles) was substituted for the adenine PNA monomer.

EXAMPLE 64

Mixed Monomer Method of Generating H$_2$N-Gly-XT-Lys-NH$_2$

In a shaker flask 25 mg of Boc Lys-MBHA resin was washed with 1 ml DMF for 15 minutes followed by 1 ml of DCM for 15 minutes. The resin was then washed three times with 1:1 DCM:DMF for 1 minute. The resin was then shaken with 0.33 ml of DCM and 1 ml of TFA/m-cresol for 2 minutes, repeated three times. The resin was then washed three times with DCM:DMF, 1 ml for 1 minute, followed by four washes with 1 ml of pyr for 1 minute. In a separate vial 26 mg of thymine PNA monomer was dissolved in 0.5 ml of DMF:pyr along with 19 mg of TBTU. To the solution was then added 23 μl of DIEA and the vial allowed to sit for 1 minute prior to adding to the resin. The reaction was shaken for 20 minutes, and a Kaiser test performed. The standard capping procedure was followed using 50 mg of Rapoport's Reagent in 1 ml of DMF. The resin was then washed with four 1 ml portions of pyridine followed by three portions of DCM:DMF. Cleavage of the protecting group was accomplished with two 1 ml portions of TFA:m-cresol for 2 minutes. The resin was washed as above. In a small vial the following PNA monomers and activators were dissolved:

| | |
|---|---|
| Adenine | 8.8 mg 17 μmoles |
| Cytosine | 8.4 mg 17 μmoles |
| Guanine | 9.1 mg 17 μmoles |
| Thymine | 6.5 mg 17 μmoles |
| TBTU | 19 mg 59 μmoles |
| DIEA | 23 ml 240 μmoles |

After standing for one minute the solution was added to the resin and shaken for 20 minutes. The resin was washed and a Kaiser test revealed the reaction to be complete. The resin was again capped with 50 mg Rapoport's reagent and washed as above. Cleavage of the protecting group with two portions of TFA:m-cresol and washing allowed the oligomer to be completed by coupling with 30 mg of glycine, 52 mg of TBTU, and 46 ml of DIEA in the usual fashion.

Cleavage of first the protecting groups and then the oligomer from the resin was accomplished as in Example 60, but with using one third of the volumes of the cleavage reagents. The oligomer was then analyzed by HPLC using the identical conditions found in Example 60. The concentration of the components, as determined using Beer's Law and the molar extinction coefficients of RNA, are found below:

H2N-Gly-AT-Lys-NH2 0.0342 mMol
H2N-Gly-CT-Lys-NH2 0.0142 mMol
H2N-Gly-GT-Lys-NH2 0.0406 mMol
H2N-Gly-TT-Lys-NH2 0.0344 mMol

The oligomers eluted from the column in the following order:

H2N-Gly-CT-Lys-NH$_2$, 16.0 minutes;
H2N-Gly-TT-Lys-NH$_2$, 17.8 minutes;
H2N-Gly-GT-Lys-NH$_2$, 19.3 minutes; and
H2N-Gly-AT-Lys-NH$_2$, 20.6 minutes.

EXAMPLE 65

Mixed Resin Synthesis of H$_2$N-aa-XX-Lys-Resin

Each of four shaker flasks were loaded with 150 mg of lysine MBHA resin. The resin was washed with 5 ml of DMF for 15 minutes, followed by 5 ml of DCM for 15 minutes. The resin was then washed with three 5 ml portions of 1:1 DCM:DMF for 1 minute each. Each of the flasks were then shaken for 2 minutes with 2 ml of DCM and 5 ml of TFA/m-cresol, this was repeated three times. The resin was then washed with three 5 ml portions of DCM:DMF, followed by four 5 ml portions of pyr. In separate vials each of the following PNA monomers were dissolved in 4 ml of 1:1 DMF:pyr in the following quantities:

| | |
|---|---|
| Adenine | 212 mg 400 μmoles |
| Cytosine | 202 mg 400 μmoles |
| Guanine | 218 mg 400 μmoles |
| Thymine | 155 mg 400 μmoles |
| In each of the vials there was also added: | |
| TBTU | 116 mg 360 μmoles |
| DIEA | 150 ml 1564 μmoles |

After activating for 1 minute, the monomers were poured into the flasks containing the resins and coupled for 20 minutes. At the end of this time the resins were drained and washed with four 5 ml portions of pyr. Kaiser tests of all 4 reactions were negative and the resins were capped with 300 mg of Rapoport's reagent in 5 ml of DMF for 5 minutes. After washing with three 5 ml portions of pyr the resin was washed with three 5 ml portions of DCM:DMF. The resins were then combined and vortexed in a 50 ml centrifuge tube for 2 minutes in a mixture of 1:1 Methanol:DCM. The resins were then filtered and dried. The dry resin was weighed and divided into 4 equal portions weighing 156 mg each. The Boc protection was removed with two 5 ml portions of TFA:m-cresol for 2 minutes each. The resin was then washed with three 5 ml portions of DMF:DCM followed by four 5 ml portions of pyr. The coupling procedure found above was repeated using identical portions of monomers. Upon completion of the coupling and capping the resins were again combined and vortexed for 2 minutes, dried and split into 4 equal portions weighing 190 mg. Each of the 4 portions was coupled with one of the following amino acids to give four pools with a known amino acid at the third position:

| | |
|---|---|
| Aspartic Acid | 130 mg 400 μmoles |
| Glycine | 70 mg 400 μmoles |
| Lysine | 153 mg 400 μmoles |
| Phenylalanine | 106 mg 400 μmoles |
| TBTU | 116 mg 160 μmoles |
| DIEA | 150 ml 1564 μmoles |

This gave 4 pools of resin containing the following sequences:

Asp-XX-Lys-Resin
Gly-XX-Lys-Resin
Lys-XX-Lys-Resin
Phe-XX-Lys-Resin

EXAMPLE 66
Synthesis of H$_2$N-XX-Asp-XX-Lys-NH$_2$ Library

After coupling the portion containing the Asp-XX-Lys-Resin from Example 65 was divided into four portions of equal size weighing 47 mg. These pools were deprotected using two 3 ml portions of TFA:m-cresol. The resins were washed and coupled using the procedure found in Example 47 using the following quantities in four vials, each containing one of the PNA monomers:

| | | |
|---|---|---|
| Adenine | 55 mg | 104 μmoles |
| Cytosine | 50 mg | 104 μmoles |
| Guanine | 55 mg | 104 μmoles |
| Thymine | 40 mg | 104 μmoles |

The following were added to each vial:

| | | |
|---|---|---|
| TBTU | 30 mg | 94 μmoles |
| DIEA | 40 ml | 417 μmoles |

After the coupling, capping, and washing the resins were combined and vortexed for 2 minutes. The resin was filtered, dried and again split into 4 equal portions weighing 55 mg and the above coupling process repeated. The resin was again deprotected and the sequence finished by coupling 45 mg, 257 μmoles of glycine, 80 mg of TBTU, 249 μmoles, and 80 ml, 835 μmoles of DIEA. The four portions of resin were combined and cleaved using the procedure found in Example 60, with the following quantities:

Step 1: m-cresol 0.66 ml
  Dimethyl Sulfide 2.0 ml
  TFA 3.66 ml
  TFMSA 0.334 ml
Step 2: m-cresol 0.835 ml
  TFA 6.66 ml
  TFMSA 0.834 ml After the cleavage from the resin was complete the solution was drained into 100 ml of ethyl ether. The white precipitate was filtered off and washed with ether. The white solid was dried, weighed and taken up in 5 ml of water. The pool of 264 compounds was desalted on a preparative Bonda-Pak Phenyl column eluting with 0.1 M ammonium acetate at pH=6 with 0.1% hexafluoroisopropanol. The column was washed with water for 10 minutes and then eluted with an acetonitrile gradient from 0–20% in 20 minutes collecting all peaks that elute.

EXAMPLE 67
Synthesis of H$_2$N-XX-Gly-XX-Lys-NH$_2$ Library

This pool was synthesized and analysed as per the procedure of Example 66.

EXAMPLE 68
Synthesis of H$_2$N-XX-Lys-XX-Lys-NH$_2$ Library

This pool was synthesized and analysed as per the procedure of Example 66.

EXAMPLE 69
Synthesis of H$_2$N-XX-Phe-XX-Lys-NH$_2$ Library

This pool was synthesized and analysed as per the procedure of Example 66.

What is claimed is:

1. A method of synthesis of a peptide nucleic acid on an activated solid phase synthesis resin comprising the steps of:
   a) treating said activated solid phase synthesis resin with a monoprotected diamine synthon to form a first synthon bound to said resin and where said first synthon includes as an integral part thereof, a secondary amine and a protected primary amine;
   b) deprotecting said first synthon to form a second synthon having as an integral part thereof said secondary amine and a free amine;
   c) treating said second synthon with a 2-haloacetic acid ester to form a third synthon having as an integral part thereof said secondary amine and an acetyl ester;
   d) treating said third synthon with a 1-haloacetylnucleobase to form a fourth synthon having as an integral part thereof a covalently bound acetylnucleobase and said acetyl ester;
   e) deprotecting said fourth synthon to form a fifth synthon having as an integral part thereof a free carboxylic acid and said covalently bound acetylnucleobase;
   f) treating said fifth synthon with a further monoprotected diamine synthon forming an extended first synthon;
   g) repeating steps f, b, c, d, and e until said peptide nucleic acid is of desired length; and
   h) terminating said synthesis at step d or e.

2. The method of claim 1 wherein the halogen group of said 2-haloacetic acid ester is Cl,Br,I, or F.

* * * * *